(12) United States Patent
Sciotti et al.

(10) Patent No.: US 6,410,728 B1
(45) Date of Patent: Jun. 25, 2002

(54) OXAZOLIDINONE CHEMOTHERAPEUTIC AGENTS

(75) Inventors: Richard J. Sciotti, Gurnee; Stevan W. Djuric, Libertyville; Marina Pliushchev, Vernon Hills, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/884,735

(22) Filed: Jun. 19, 2001

Related U.S. Application Data

(63) Continuation-in-part of application No. 09/652,504, filed on Aug. 31, 2000, now Pat. No. 6,277,868.

(51) Int. Cl.[7] ............ C07D 487/02; C07D 413/10; C07D 277/68

(52) U.S. Cl. ............ 544/256; 544/335; 546/271.4; 548/180; 548/232

(58) Field of Search ................ 548/232, 180; 544/256, 335; 546/271.4

(56) References Cited

FOREIGN PATENT DOCUMENTS

WO    WO 93/09103    *   5/1993

\* cited by examiner

*Primary Examiner*—Floyd D. Higel
*Assistant Examiner*—Andrea D. Small
*(74) Attorney, Agent, or Firm*—B. Gregory Donner

(57) ABSTRACT

Compounds of the formula

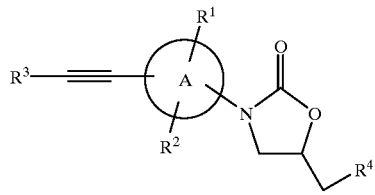

or therapeutically acceptable salts or prodrugs thereof, are useful for treating bacterial infections, psoriasis, arthritis, and toxicity due to chemotherapy. Preparation of the compounds, compositions containing the compounds, and treatment of diseases using the compounds are disclosed.

1 Claim, No Drawings

OXAZOLIDINONE CHEMOTHERAPEUTIC AGENTS

CROSS REFERENCE TO RELATED APPLICATIONS

This application is a continuation-in-part of pending U.S. application Ser. No. 09/652,504, filed Aug. 31, 2000 now U.S. Pat. No. 6,277,868.

TECHNICAL FIELD

This invention is directed to compounds useful for treating bacterial infections, psoriasis, arthritis, and toxicity due to chemotherapy; preparation of the compounds; chemotherapeutic compositions comprising the compounds; and methods for treating diseases using the compounds.

BACKGROUND OF THE INVENTION

The escalation of resistance to antibiotics once useful for treatment of bacterial infections resulting from pathogens such as *Staphylococcus aureus*, *Staphylococcus epidermidis*, and *Enterococcus faecium* is problematic in the United States and Europe (*Drugs Exp. Clin. Res.* 1994, XX, 215–224; *Am. J. Surg.* 1995, 5A (Suppl.), 8S-12S; *Drugs*, 1994, 48, 678–688; and *Current Pharmaceutical Design*, 1996, Vol.2, No.2, 175–194). Thus, the development of new broad-spectrum synthetic and semi-synthetic antibacterial compounds is the subject of constant current research.

One such class of compounds are synthetic oxazolidinones, exemplified by eperezolid and linezolid, which constitute a class of orally active, synthetic antibacterial agents (*Current Pharmaceutical Design*, op. cit.).

U.S. Pat. No. 6,040,306, the disclosure of which is hereinafter incorporated by reference into this specification, also teaches the use of oxazolidinones for treatment of psoriasis, arthritis, and toxicity due to chemotherapy.

Given these and other reports on the therapeutic benefit of oxazolidinone antibacterials, the loss of activity among antibacterials which were once efficacious for treatment of certain Gram-positive bacteria, and the continuing need for treatment of a diseases such as psoriasis, arthritis, and toxicity due to chemotherapy, there is a continuing need for the development of novel oxazolidinone drugs with modified or improved profiles of activity.

SUMMARY OF THE INVENTION

In another embodiment, the instant invention is directed to compounds which can be useful for treating bacterial infections, psoriasis, arthritis, and toxicity due to chemotherapy, said compounds having structural formula (I)

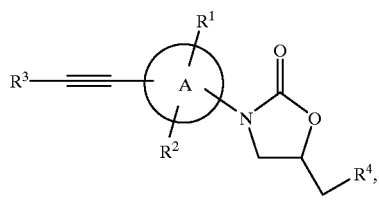

(I)

or therapeutically acceptable salts or prodrugs thereof, wherein

A is selected from
(a) phenyl,
(b) a five-membered aromatic ring containing one or two atoms selected from N, O, and S, and the remaining atoms are carbon,
wherein the groups defining (b) are substituted on a substitutable carbon or nitrogen atom in the ring, and
(c) a six-membered aromatic ring containing one or two nitrogen atoms, and the remaining atoms are carbon; wherein the groups defining (c) are substituted on a substitutable carbon atom in the ring;

$R^1$ and $R^2$ are independently selected from hydrogen, alkyl, cycloalkyl, hydroxy, amino, halo, haloalkyl, and perfluoroalkyl;

$R^3$ is selected from
(a) alkyl, alkanoyl, carboxamido, cycloalkyl, cyclothioalkoxy, cycloalkylsulfinyl, cycloalkoxycarbonyl, alkylsulfonyl, alkoxycarbonyl, cycloalkenyl, cycloalkenylsulfonyl,
wherein the groups defining (a) can be optionally substituted with 1–5 substituents independently selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle,
(b) aryl, arylalkyl, arylthio, arylsulfinyl, aryloxycarbonyl, heteroaryl, heteroarylalkyl, heteroarylsulfonyl, heteroaryloxycarbonyl, heterocycle, (heterocycle)alkyl, (heterocycle)sulfonyl, and (heterocycle)oxycarbonyl,
wherein the groups defining (b) can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle,
wherein for the groups defining (a) and (b), the substituted aryl, the substituted heteroaryl, and the substituted heterocycle are substituted with 1–5 substituents independently selected from alkyl, alkoxy, carboxy, azido, carboxaldehyde, halo, hydroxy, perfluoroalkyl, perfluoroalkoxy, and amino;

$R^4$ is selected from $NHR^5$, $N(R^6)C(O)OR^7$, $N(R^6)C(O)N(R^6)_2$, $OR^7$, $SR^7$, $S(O)R^7$, and $SO_2R^7$;

$R^5$ is selected from alkanoyl, aryloyl, thioalkanoyl, heteroaryl, heteroarylalkyl, (heteroaryl)oyl, heterocycle, and (heterocycle)alkyl,
wherein the groups defining $R^5$ can be optionally substituted with 1–5 substituents independently selected from alkyl, alkoxy, carboxy, azido, carboxaldehyde, halo, hydroxy, perfluoroalkyl, perfluoroalkoxy, and amino;

$R^6$ is selected from
  (a) hydrogen,
  (b) alkyl,
    wherein the alkyl can be optionally substituted with 1–5 substituents independently selected from alkoxy, carboxy, azido, carboxaldehyde, halo, hydroxy, perfluoroalkyl, and perfluoroalkoxy;
  (c) cycloalkyl, cycloalkylalkyl, aryl, heteroaryl, heteroarylalkyl, heterocycle, and (heterocycle)alkyl;
    wherein the groups defining (c) can be optionally substituted with 1–5 substituents independently selected from alkyl, alkoxy, carboxy, azido, carboxaldehyde, halo, hydroxy, perfluoroalkyl, perfluoroalkoxy, and amino; and $R^7$ is selected from
  (a) alkyl,
    wherein the alkyl can be optionally substituted with 1–5 substituents independently selected from alkoxy, carboxy, azido, carboxaldehyde, halo, hydroxy, perfluoroalkyl, and perfluoroalkoxy,
  (b) cycloalkyl, cycloalkylalkyl, aryl, heteroaryl, heteroarylalkyl, heterocycle, and (heterocycle)alkyl;
    wherein the groups defining (b) can be optionally substituted with 1–5 substituents independently selected from alkyl, alkoxy, carboxy, azido, carboxaldehyde, halo, hydroxy, perfluoroalkyl, and perfluoroalkoxy,
    all of the foregoing with the proviso that when A is phenyl and $R^4$ is $NHR^5$ wherein $R^5$ is alkanoyl, $R^3$ is not unsubstituted alkyl; and
    with the proviso that when A is phenyl and $R^4$ is methoxy, $R^3$ is not optionally substituted phenyl.

In another embodiment, the instant invention is directed to compounds which can be useful for treating bacterial infections, psoriasis, arthritis, and toxicity due to chemotherapy, said compounds having structural formula (I)

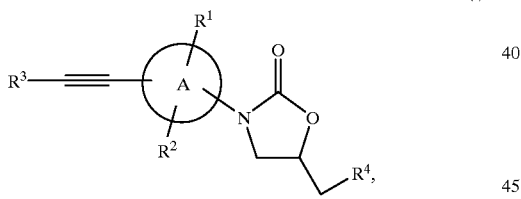

(I)

or therapeutically acceptable salts or prodrugs thereof, wherein
  A is selected from
    (a) phenyl,
    (b) a five-membered aromatic ring containing one or two atoms selected from N, O, and S, and the remaining atoms are carbon,
      wherein the groups defining (b) are substituted on a substitutable carbon or nitrogen atom in the ring, and
    (c) a six-membered aromatic ring containing one or two nitrogen atoms, and the remaining atoms are carbon;
      wherein the groups defining (c) are substituted on a substitutable carbon atom in the ring;
  $R^1$ and $R^2$ are independently selected from hydrogen, alkyl, cycloalkyl, hydroxy, amino, halo, haloalkyl, and perfluoroalkyl;
  $R^3$ is selected from
    (a) alkyl, alkanoyl, carboxamido, cycloalkyl, cyclothioalkoxy, cycloalkylsulfinyl, cycloalkoxycarbonyl, alkylsulfonyl, alkoxycarbonyl, cycloalkenyl, cycloalkenylsulfonyl,
      wherein the groups defining (a) can be optionally substituted with 1–5 substituents independently selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle,
    (b) aryl, arylalkyl, arylthio, arylsulfinyl, aryloxycarbonyl, heteroaryl, heteroarylalkyl, heteroarylsulfonyl, heteroaryloxycarbonyl, heterocycle, (heterocycle)alkyl, (heterocycle)sulfonyl, and (heterocycle)oxycarbonyl,
      wherein the groups defining (b) can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl, thioalkoxy, thioalkoxyalkyl, thioalkoxyalkenyl, unsubstituted or substituted aryl, unsubstituted or substituted heteroaryl, and unsubstituted or substituted heterocycle,
    wherein for the groups defining (a) and (b), the substituted aryl, the substituted heteroaryl, and the substituted heterocycle are substituted with 1–5 substituents independently selected from alkyl, alkoxy, carboxy, azido, carboxaldehyde, halo, hydroxy, perfluoroalkyl, perfluoroalkoxy, and amino;

$R^4$ is selected from $NHR^5$, $N(R^6)C(O)OR^7$, $N(R^6)C(O)N(R^6)_2$, $OR^7$, $SR^7$, $S(O)R_7$, and $SO_2R^7$;

$R^5$ is selected from alkanoyl, aryloyl, thioalkanoyl, heteroaryl, heteroarylalkyl, (heteroaryl)oyl, heterocycle, and (heterocycle)alkyl,
  wherein the groups defining $R^5$ can be optionally substituted with 1–5 substituents independently selected from alkyl, alkoxy, carboxy, azido, carboxaldehyde, halo, hydroxy, perfluoroalkyl, perfluoroalkoxy, and amino;

$R^6$ is selected from
  (a) hydrogen,
  (b) alkyl,
    wherein the alkyl can be optionally substituted with 1–5 substituents independently selected from alkoxy, carboxy, azido, carboxaldehyde, halo, hydroxy, perfluoroalkyl, and perfluoroalkoxy;
  (c) cycloalkyl, cycloalkylalkyl, aryl, heteroaryl, heteroarylalkyl, heterocycle, and (heterocycle)alkyl;
    wherein the groups defining (c) can be optionally substituted with 1–5 substituents independently selected from alkyl, alkoxy, carboxy, azido, carboxaldehyde, halo, hydroxy, perfluoroalkyl, perfluoroalkoxy, and amino; and R⁷ is selected from
(a) alkyl,
  wherein the alkyl can be optionally substituted with 1–5 substituents independently selected from alkoxy, carboxy, azido, carboxaldehyde, halo, hydroxy, perfluoroalkyl, and perfluoroalkoxy,
(b) cycloalkyl, cycloalkylalkyl, aryl, heteroaryl, heteroarylalkyl, heterocycle, and (heterocycle)alkyl;
  wherein the groups defining (b) can be optionally substituted with 1–5 substituents independently selected from alkyl, alkoxy, carboxy, azido, carboxaldehyde, halo, hydroxy, perfluoroalkyl, and perfluoroalkoxy.

DETAILED DESCRIPTION OF THE INVENTION

The compounds of this invention are substituted oxazolidinones which are useful for treating bacterial infections, psoriasis, arthritis, toxicity due to chemotherapy, and obesity. In its principle embodiment, the invention is directed to compounds of formula (I)

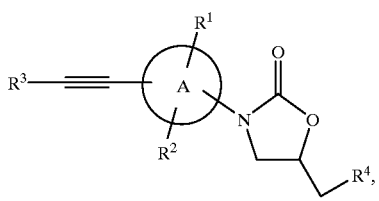

(I)

or therapeutically acceptable salts thereof, wherein A, $R^1$, $R^2$, $R^3$ and $R_4$ are defined hereinabove.

The compounds of the invention comprise oxazolidinones connected through the nitrogen atom in the oxazolidinone ring to a substituted alkyne through ring A. Ring A is a stable, aromatic, monocyclic group substituted through carbon atoms in the ring. Preferably, ring A is phenyl, although heteroaryl rings such as furanyl, thienyl, pyrrolyl, oxazolyl, thiazolyl, imidazolyl, pyrazolyl, isoxazolyl, isothiazolyl, pyridyl, pyridazinyl, pyrimidinyl, and pyrazinyl are within the scope of the invention. Ring A can be further substituted by independent replacement of one or two hydrogen atoms thereon by substituents defined by $R^1$ and $R^2$ so that, for instance and by way of example only, ring A can be substituted by halo, preferably fluorine. Lines drawn into ring A (such as from $R^1$ and $R^2$) indicate that the bonds can be attached to any substitutable ring carbon atom. Preferred substituents include, but are not limited to, alkoxycarbonyl, halo, and the like.

It is intended that the definition of any substituent or variable at a particular location in a molecule be independent of its definition elsewhere in that molecule. For example, for substituents defined by $R^4$, it is intended that the definition of an $R^4$ substituent at one location is independent of its definition elsewhere. Thus, $N(R^6)C(O)N(R^6)_2$ represents, for instance, and by way of example only, $N(CH_3)C(O)N(C_2H_5)(C_3H_7)$, and the like. In a preferred embodiment of the invention, $R^4$ is $NHR^5$ wherein $R^5$ is alkanoyl, preferably acetyl.

It is believed that when the compounds have attached thereto a hydroxyl, amino, or carboxylic acid group, prodrugs can be prepared from these compounds by attaching thereto a prodrug-forming group to provide prodrug esters prodrug amides, and prodrug esters, respectively. These prodrugs can then be rapidly transformed in vivo to the parent compound, such as, for example, by hydrolysis in blood. The term "therapeutically acceptable prodrug," as used herein, refers to those prodrugs of the compounds which are suitable for use in contact with the tissues of humans and lower animals with undue toxicity, irritation, allergic response, and the like, commensurate with a reasonable benefit/risk ratio, and effective for their intended use, as well as the zwitterionic forms, wherein possible, of the compounds.

The invention is based, in part, on the structure activity relationship data provided hereinbelow. Therefore, another embodiment of the invention encompasses any compound, including metabolic precursors of the inhibitor compounds, which contain an essential inhibitory group as disclosed herein. These inhibitory groups can be in masked form or prodrug form and can be released by metabolic or other processes after administration to a patient.

Because asymmetric centers exist in the compounds, the invention contemplates stereoisomers and mixtures thereof Individual stereoisomers of compounds are prepared by synthesis from starting materials containing the chiral centers or by preparation of mixtures of enantiomeric products followed by separation such as conversion to a mixture of diastereomers followed by separation or recrystallization, chromatographic techniques, or direct separation of the enantiomers on chiral chromatographic columns. Starting compounds of particular stereochemistry are either commercially available or are made by the methods described below and resolved by techniques well-known in the art.

Because carbon—carbon double bonds may also exist in the compounds, the invention contemplates various geometric isomers and mixtures thereof resulting from the arrangement of substituents around these carbon—carbon double bonds. These substituents are designated as being in the E or Z configuration wherein the term "E" refers to higher order substituents on opposite sides of the carbon—carbon double bond, and the term "Z" refers to higher order substituents on the same side of the carbon-carbon double bond. A thorough discussion of E and Z isomerism is provided in *Advanced Organic Chemistry. Reactions, Mechanisms, and Structure*, 4th ed., John Wiley & Sons, New York, 1992, pp. 109–112.

Accordingly, it will be seen by those skilled in the art that another embodiment of compounds of formula (I) are compounds of formula (II)

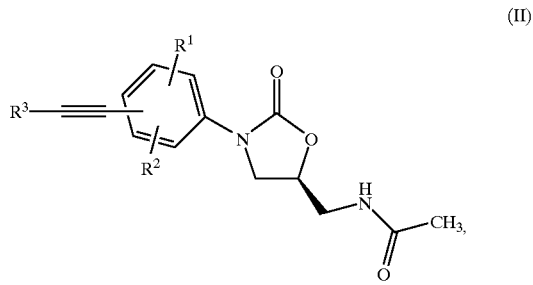

(II)

or therapeutically acceptable salts or prodrugs or thereof, wherein $R^1$, $R^2$, and $R^3$ are defined hereinabove.

In another embodiment of the invention is disclosed a composition comprising a compound of formula (I) or formula (II), or a therapeutically acceptable salt or prodrug thereof, and a therapeutically acceptable excipient.

In another embodiment of the invention is disclosed a composition comprising a compound of formula (I) or formula (II), or a therapeutically acceptable salt or prodrug thereof, and a therapeutically acceptable excipient.

In another embodiment of the invention is disclosed a method for treating bacterial infections, psoriasis, arthritis, and toxicity due to chemotherapy in a patient comprising administering to the patient a therapeutically acceptable amount of a compound of formula (I)

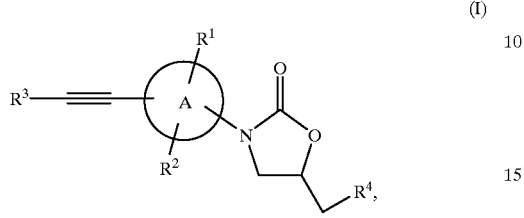

(I)

or a therapeutically acceptable salt or prodrug thereof, wherein
A is selected from
  (a) phenyl,
  (b) a five-membered aromatic ring containing one or two atoms selected from N, O, and S, and the remaining atoms are carbon,
    wherein the groups defining (b) are substituted on a substitutable carbon or nitrogen atom in the ring, and
  (c) a six-membered aromatic ring containing one or two nitrogen atoms, and the remaining atoms are carbon;
    wherein the groups defining (c) are substituted on a substitutable carbon atom in the ring;
$R^1$ and $R^2$ are independently selected from hydrogen, alkyl, cycloalkyl, hydroxy, amino, halo, haloalkyl, and perfluoroalkyl;
$R^3$ is selected from
  (a) alkyl, alkanoyl, carboxamido, cycloalkyl, cyclothioalkoxy, cycloalkylsulfinyl, cycloalkoxycarbonyl, alkylsulfonyl, alkoxycarbonyl, cycloalkenyl, cycloalkenylsulfonyl,
    wherein the groups defining (a) can be optionally substituted with 1–5 substituents independently selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle,
  (b) aryl, arylalkyl, arylthio, arylsulfinyl, aryloxycarbonyl, heteroaryl, heteroarylalkyl, heteroarylsulfonyl, heteroaryloxycarbonyl, heterocycle, (heterocycle)alkyl, (heterocycle)sulfonyl, and (heterocycle)oxycarbonyl,
    wherein the groups defining (b) can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle,
    wherein for the groups defining (a) and (b), the substituted aryl, the substituted heteroaryl, and the substituted heterocycle are substituted with 1–5 substituents independently selected from alkyl, alkoxy, carboxy, azido, carboxaldehyde, halo, hydroxy, perfluoroalkyl, perfluoroalkoxy, and amino;
$R^4$ is selected from $NHR^5$, $N(R^6)C(O)OR^7$, $N(R^6)C(O)N(R^6)_2$, $OR^7$, $SR^7$, $S(O)R^7$, and $SO_2R^7$;
$R^5$ is selected from alkanoyl, aryloyl, thioalkanoyl, beteroaryl, heteroarylalkyl, (heteroaryl)oyl, heterocycle, and (heterocycle)alkyl,
    wherein the groups defining $R^5$ can be optionally substituted with 1–5 substituents independently selected from alkyl, alkoxy, carboxy, azido, carboxaldehyde, halo, hydroxy, perfluoroalkyl, perfluoroalkoxy, and amino;
$R^6$ is selected from
  (a) hydrogen,
  (b) alkyl,
    wherein the alkyl can be optionally substituted with 1–5 substituents independently selected from alkoxy, carboxy, azido, carboxaldehyde, halo, hydroxy, perfluoroalkyl, and perfluoroalkoxy;
  (c) cycloalkyl, cycloalkylalkyl, aryl, heteroaryl, heteroarylalkyl, heterocycle, and (heterocycle)alkyl;
    wherein the groups defining (c) can be optionally substituted with 1–5 substituents independently selected from alkyl, alkoxy, carboxy, azido, carboxaldehyde, halo, hydroxy, perfluoroalkyl, perfluoroalkoxy, and amino; and
$R^7$ is selected from
  (a) alkyl,
    wherein the alkyl can be optionally substituted with 1–5 substituents independently selected from alkoxy, carboxy, azido, carboxaldehyde, halo, hydroxy, perfluoroalkyl, and perfluoroalkoxy,
  (b) cycloalkyl, cycloalkylalkyl, aryl, heteroaryl, heteroarylalkyl, heterocycle, and (heterocycle)alkyl;
    wherein the groups defining (b) can be optionally substituted with 1–5 substituents independently selected from alkyl, alkoxy, carboxy, azido, carboxaldehyde, halo, hydroxy, perfluoroalkyl, and perfluoroalkoxy.
all of the foregoing with the proviso that when A is phenyl and $R^4$ is $NHR^5$ wherein $R^5$ is alkanoyl, $R^3$ is not unsubstituted alkyl.

In another embodiment of the invention is disclosed a method for treating bacterial infections, psoriasis, arthritis, and toxicity due to chemotherapy in a patient comprising administering to the patient a therapeutically acceptable amount of a compound of formula (I)

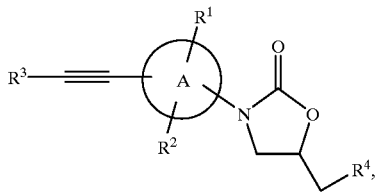

(I)

or a therapeutically acceptable salt or prodrug thereof, wherein
A is selected from
(a) phenyl,
(b) a five-membered aromatic ring containing one or two atoms selected from N, O, and S, and the remaining atoms are carbon,
wherein the groups defining (b) are substituted on a substitutable carbon or nitrogen atom in the ring, and
(c) a six-membered aromatic ring containing one or two nitrogen atoms, and the remaining atoms are carbon;
wherein the groups defining (c) are substituted on a substitutable carbon atom in the ring;
$R^1$ and $R^2$ are independently selected from hydrogen, alkyl, cycloalkyl, hydroxy, amino, halo, haloalkyl, and perfluoroalkyl;
$R^3$ is selected from
(a) alkyl, alkanoyl, carboxamido, cycloalkyl, cyclothioalkoxy, cycloalkylsulfinyl, cycloalkoxycarbonyl, alkylsulfonyl, alkoxycarbonyl, cycloalkenyl, cycloalkenylsulfonyl,
wherein the groups defining (a) can be optionally substituted with 1–5 substituents independently selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle,
(b) aryl, arylalkyl, arylthio, arylsulfinyl, aryloxycarbonyl, heteroaryl, heteroarylalkyl, heteroarylsulfonyl, heteroaryloxycarbonyl, heterocycle, (heterocycle)alkyl, (heterocycle)sulfonyl, and (heterocycle)oxycarbonyl,
wherein the groups defining (b) can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle,
wherein for the groups defining (a) and (b), the substituted aryl, the substituted heteroaryl, and the substituted heterocycle are substituted with 1–5 substituents independently selected from alkyl, alkoxy, carboxy, azido, carboxaldehyde, halo, hydroxy, perfluoroalkyl, perfluoroalkoxy, and amino;
$R^4$ is selected from $NHR^5$, $N(R^6)C(O)OR^7$, $N(R^6)C(O)N(R^6)_2$, $OR^7$, $SR^7$, $S(O)R^7$, and $SO_2R^7$;
$R^5$ is selected from alkanoyl, aryloyl, thioalkanoyl, heteroaryl, heteroarylalkyl, (heteroaryl)oyl, heterocycle, and (heterocycle)alkyl,
wherein the groups defining $R^5$ can be optionally substituted with 1–5 substituents independently selected from alkyl, alkoxy, carboxy, azido, carboxaldehyde, halo, hydroxy, perfluoroalkyl, perfluoroalkoxy, and amino;
$R^6$ is selected from
(a) hydrogen,
(b) alkyl,
wherein the alkyl can be optionally substituted with 1–5 substituents independently selected from alkoxy, carboxy, azido, carboxaldehyde, halo, hydroxy, perfluoroalkyl, and perfluoroalkoxy;
(c) cycloalkyl, cycloalkylalkyl, aryl, heteroaryl, heteroarylalkyl, heterocycle, and (heterocycle)alkyl;
wherein the groups defining (c) can be optionally substituted with 1–5 substituents independently selected from alkyl, alkoxy, carboxy, azido, carboxaldehyde, halo, hydroxy, perfluoroalkyl, perfluoroalkoxy, and amino; and
$R^7$ is selected from
(a) alkyl,
wherein the alkyl can be optionally substituted with 1–5 substituents independently selected from alkoxy, carboxy, azido, carboxaldehyde, halo, hydroxy, perfluoroalkyl, and perfluoroalkoxy,
(b) cycloalkyl, cycloalkylalkyl, aryl, heteroaryl, heteroarylalkyl, heterocycle, and (heterocycle)alkyl;
wherein the groups defining (b) can be optionally substituted with 1–5 substituents independently selected from alkyl, alkoxy, carboxy, azido, carboxaldehyde, halo, hydroxy, perfluoroalkyl, and perfluoroalkoxy.

The present invention is also directed to compounds selected from the group consisting of:
N-(((5S)-3-(3-fluoro-4-(4-(carbomethoxyphenyl)ethynyl)phenyl)-2-oxo-1,3-oxazolidin-5-yl)methyl)acetamide,
N-(((5S)-3-(3-fluoro-4-(1H-pyrrol-2-ylethynyl)phenyl)-2-oxo-1,3-oxazolidin-5-yl)methyl)acetamide,
N-(((5S)-3-(3-fluoro-4-(7H-purin-6-ylethynyl)phenyl)-2-oxo-1,3-oxazolidin-5-yl)methyl)acetamide,
N-(((5S)-3-(4-((5-(aminosulfonyl)thien-2-yl)ethynyl)-3-fluorophenyl)-2-oxo-1,3-oxazolidin-5-yl)methyl)acetamide,
N-(((5S)-3-(3-fluoro-4-((1-oxo-2,3-dihydro-1H-inden-5-yl)ethynyl)phenyl)-2-oxo-1,3-oxazolidin-5-yl)methyl)acetamide,
5-((4-((5S)-5-((acetylamino)methyl)-2-oxo-1,3-oxazolidin-3-yl)-2-fluorophenyl)ethynyl)-2,3-dihydro-1-benzofuran-7-carboxylic acid,
N-(((5S)-3-(4-((1,3-dioxo-2,3-dihydro-1H-isoindol-5-yl)ethynyl)-3-fluorophenyl)-2-oxo-1,3-oxazolidin-5-yl)methyl)acetamide, N-(((S)-3-(4-((5-cyanopyridin-3-yl)ethynyl)-3-fluorophenyl)-2-oxo-1,3-oxazolidin-5-yl)methyl)acetamide, N-(((5S)-3-(3-fluoro-4-(1,8-naphthyridin-2-ylethynyl)phenyl)-2-oxo-1,3-oxazolidin-5-yl)methyl)acetamide, N-(((5S)-3-(3-fluoro-4-((4-(hydroxymethyl)phenyl)ethyny)phenyl)-2-oxo-1,3-oxazolidin-5-yl)methyl)acetamide, N-(((5S)-3-(3-fluoro-4-(1,8-naphthyridin-2-ylethynyl)phenyl)-2-oxo-1,3-oxazolidin-3,5-yl)methyl)acetamide, N-(((5S)-3-(3-fluoro-4-((4-methoxy-3-pyridinyl)ethynyl)phenyl)-2-oxo-1,3-oxazolidin-5-yl)methyl)acetamide, N-(((5S)-3-(4-((2-aminopyrimidin-5-yl)ethyny)-3-fluorophenyl)-2-oxo-1,3-oxazolidin-5-yl)methyl)acetamide, N-(((5S)-3-(3-fluoro-4-(pyrimidin-5-ylethynyl)phenyl)-2-oxo-1,3-oxazolidin-5-yl)methyl)acetamide, N-(((S)-3-(4-((3-aminophenyl)ethynyl)-3-fluorophenyl)-2-oxo-1,3-oxazolidin-5-yl)methyl)acetamide, methyl 3-((4-((5S)-5-((acetylamino)methyl)-2-oxo-1,3-oxazolidin-3-yl)-2-fluorophenyl)ethynyl)benzoate, N-(3-(2-(4-((5S)-5-((acetylamino)methyl)-2-oxo-1,3-oxazolidin-3-yl)-2-fluorophenyl)ethynyl)phenyl)acetamide, N-(((5S)-3-(4-((3-(aminomethyl)phenyl)ethynyl)-3-fluorophenyl)-2-oxo-1,3-oxazolidin-5-yl)methyl)acetamide, N-(((5S)-3-(3-fluoro-4-((4-hydroxyphenyl)ethynyl)phenyl)-2-oxo-1,3-oxazolidin-5-yl)methyl)acetamide, and N-(((5S)-3-(3-fluoro-4-((2-oxo-2,3-dihydro-1,3-benzothiazol-6-yl)ethynyl)phenyl)-2-oxo-1,3-oxazolidin-5-yl)methyl)acetamide.

As used throughout the specification, the following terms have the meanings indicated:

The term "alkanoyl," as used herein, refers to an alkyl group, as defined herein, attached to the parent molecular group through a carbonyl group.

The term "alkanoyloxy," as used herein, refers to an alkanoyl group, as defined herein, attached to the parent molecular group through an oxygen atom.

The term "alkanoyloxyalkyl," as used herein, refers to an alkyl group, as defined herein, to which is attached at least one alkanoyloxy substituent.

The term "alkanoyloxyalkenyl," as used herein, refers to an alkenyl group, as defined herein, to which is attached at least one alkanoyloxy substituent.

The term "alkenyl," as used herein, refers to a monovalent straight or branched chain hydrocarbon having from two to six carbons and at least one carbon-carbon double bond.

The term "alkoxy," as used herein, refers to an alkyl group, as defined herein, attached to the parent molecular group through an oxygen atom.

The term "alkoxyalkyl," as used herein, refers to an alkyl group, as defined herein, to which is attached at least one alkoxy substituent.

The term "alkoxyalkenyl," as used herein, refers to an alkenyl group, as defined herein, to which is attached at least one alkoxy substituent.

The term "alkoxycarbonyl," as used herein, refers to an alkoxy group, as defined herein, attached to the parent molecular group through a carbonyl group.

The term "alkoxycarbonylalkyl," as used herein, refers to an alkyl group, as defined herein, to which is attached at least one alkoxycarbonyl substituent.

The term "alkoxycarbonylalkenyl," as used herein, refers to an alkenyl group, as defined herein, to which is attached at least one alkoxycarbonyl substituent.

The term "alkyl," as used herein, refers to a saturated, monovalent straight or branched chain hydrocarbon having from one to six carbons. The alkyl groups of this invention can be optionally substituted with 1–5 substituents selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle groups substituting the alkyl groups of this invention are substituted with at least one substituent selected from alkyl, alkoxy, carboxy, azido, carboxaldehyde, halo, hydroxy, perfluoroalkyl, and perfluoroalkoxy.

The term "alkylsulfinyl," as used herein, refers to an alkyl group, as defined herein, attached to the parent molecular group through an —S(O)— group.

The term "alkylsulfinylalkyl," as used herein, refers to an alkyl group, as defined herein, to which is attached at least one alkylsulfinyl substituent.

The term "alkylsulfinylalkenyl," as used herein, refers to an alkenyl group, as defined herein, to which is attached at least one alkylsulfinyl substituent.

The term "alkylsulfonyl," as used herein, refers to an alkyl group, as defined herein, attached to the parent molecular group through a sulfonyl group.

The term "alkylsulfonylalkyl," as used herein, refers to an alkyl group, as defined herein, to which is attached at least one alkylsulfonyl substituent.

The term "alkylsulfonylalkenyl," as used herein, refers to an alkenyl group, as defined herein, to which is attached at least one alkylsulfonyl substituent.

The term "amino," as used herein, refers to —NH$_2$ or derivatives thereof formed by independent replacement of one or both hydrogen atoms thereon with a substituent or substituents independently selected from alkyl, alkanoyl, aryl, arylalkyl, cycloalkyl, cycloalkylalkyl, heteroaryl, heteroarylalkyl, and an amino protecting group.

The term "aminoalkyl," as used herein, refers to an alkyl group, as defined herein, to which is attached at least one amino substituent.

The term "aminoalkenyl," as used herein, refers to an alkenyl group, as defined herein, to which is attached at least one amino substituent.

The terms "amino protecting group," or "nitrogen protecting group," as used herein, refer to selectively introducible and removable groups which protect amino groups against undesirable side reactions during synthetic procedures. Examples of amino protecting groups include methoxycarbonyl, ethoxycarbonyl, trichloroethoxycarbonyl, benzyloxycarbonyl (Cbz), chloroacetyl, trifluoroacetyl, phenylacetyl, benzoyl (Bn), benzyl (Bz), dimethoxybenzyl, tert-butoxycarbonyl (Boc), para-methoxybenzyloxycarbonyl, isopropoxycarbonyl, phthaloyl, succinyl, diphenylmethyl, triphenylmethyl (trityl), methanesulfonyl, para-toluenesulfonyl, trimethylsilyl, triethylsilyl, triphenylsilyl, and the like. Preferred amino or nitrogen protecting groups of this invention are phthalyl and 2,4-dimethoxybenzyl. Amino protecting group can also be used as prodrug-forming groups.

The term "aminosulfonyl," as used herein, refers to an amino group, as defined herein, attached to the parent molecular group through a sulfonyl group.

The term "arylsulfonylalkyl," as used herein, refers to an alkyl group, as defined herein, to which is attached at least one arylsulfonyl substituent.

The term "arylsulfonylalkenyl," as used herein, refers to an alkenyl group, as defined herein, to which is attached at least one arylsulfonyl substituent.

The term "aryl," as used herein, refers to groups containing at least one aromatic, carbocyclic ring. Aryl groups of this invention are exemplified by phenyl, naphthyl, indenyl, indanyl, dihydronaphthyl, tetrahydronaphthyl, and the like. The aryl groups of this invention can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. The substituted aryl, heteroaryl, and heterocycle groups substituting the aryl groups of this invention are substituted with at least one substituent selected from alkyl, alkoxy, carboxy, azido, carboxaldehyde, halo, hydroxy, perfluoroalkyl, and perfluoroalkoxy.

The term "arylalkyl," as used herein, refers to an alkyl group, as defined herein, to which is attached at least one aryl substituent.

The term "arylalkenyl," as used herein, refers to an alkenyl group, as defined herein, to which is attached at least one aryl substituent.

The term "aryloyl," as used herein, refers to an aryl group, as defined herein, attached to the parent molecular group through a carbonyl group.

The term "arylsulfinyl," as used herein, refers to an aryl group, as defined herein, attached to the parent molecular group through an —S(O)— group.

The term "arylsulfinylalkyl," as used herein, refers to an alkyl group, as defined herein, to which is attached at least one arylsulfinyl substituent.

The term "arylsulfinylalkenyl," as used herein, refers to an alkenyl group, as defined herein, to which is attached at least one arylsulfinyl substituent.

The term "arylsulfonyl," as used herein, refers to an alkyl group, as defined herein, attached to the parent molecular group through a sulfonyl group.

The term "arylsulfonylalkyl," as used herein, refers to an alkyl group, as defined herein, to which is attached at least one arylsulfonyl substituent.

The term "arylsulfonylalkenyl," as used herein, refers to an alkenyl group, as defined herein, to which is attached at least one arylsulfonyl substituent.

The term "arylthio," as used herein, refers to an aryl group, as defined herein, attached to the parent molecular group through a sulfur atom.

The term "azido," as used herein, refers to —$N_3$.

The term "carbonyl," as used herein, refers to —C(=O)—.

The term "carboxamido," as used herein, refers to an amide, e.g., an amino group, as defined herein, attached to the parent molecular group through a carbonyl group.

The term "carboxamidoalkyl," as used herein, refers to an alkyl group, as defined herein, to which is attached at least one carboxamido substituent.

The term "carboxamidoalkenyl," as used herein, refers to an alkenyl group, as defined herein, to which is attached at least one carboxamido substituent.

The term "carboxy," as used herein, refers to —$CO_2H$ or a derivative thereof formed by replacement of the hydrogen atom thereon by a carboxy protecting group.

The term "carboxyalkyl," as used herein, refers to an alkyl group, as defined herein, to which is attached at least one carboxy substituent.

The term "carboxyalkenyl," as used herein, refers to an alkenyl group, as defined herein, to which is attached at least one carboxy substituent.

The term "carboxy protecting group," as used herein, refers to selectively introducible and removable groups which protect carboxy groups against undesirable side reactions during synthetic procedures and includes all conventional carboxy protecting groups. Examples of carboxy protecting groups include methyl, ethyl, n-propyl, isopropyl, 1,1,-dimethylpropyl, n-butyl, tert-butyl, phenyl, naphthyl, benzyl, diphenylmethyl, triphenylmethyl (trityl), para-nitrobenzyl, para-methoxybenzyl, acetylmethyl, benzoylmethyl, para-nitrobenzoylmethyl, para-bromobenzoylmethyl, 2-tetrahydropyranyl, 2-tetrahydrofuranyl, 2,2,2-trichloroethyl, cyclopropyl, cyclobutyl, cyclopentyl, cyclohexyl, methoxymethyl, methoxyethoxymethyl, arylalkoxyalkyl, benzyloxymethyl, 1,1-dimethyl-2-propenyl, 3-methyl-3-butenyl, allyl, and the like. Carboxy protecting group can also be used as prodrug-forming groups.

The term "cyano," as used herein, refers to —CN.

The term "cyanoalkyl," as used herein, refers to an alkyl group, as defined herein, to which is attached at least one cyano substituent.

The term "cyanoalkenyl," as used herein, refers to an alkenyl group, as defined herein, to which is attached at least one cyano substituent.

The term "cycloalkenyl," as used herein, refers to a monovalent cyclic or bicyclic hydrocarbon of three to fifteen carbons and at least one carbon-carbon double bond.

The term "cycloalkenylsulfinyl," as used herein, refers to a cycloalkenyl group, as defined herein, attached to the parent molecular group through a —S(O)— group.

The term "cycloalkenylsulfonyl," as used herein, refers to a cycloalkenyl group, as defined herein, attached to the parent molecular group through a —$S(O)_2$— group.

The term "cycloalkoxy," as used herein, refers to a cycloalkyl group, as defined herein, attached to the parent molecular group through an oxygen atom.

The term "cycloalkoxycarbonyl," as used herein, refers to an cycloalkoxy group, as defined herein, attached to the parent molecular group through a carbonyl group.

The term "cycloalkyl," as used herein, refers to a monovalent saturated cyclic or bicyclic hydrocarbon of three to fifteen carbons. The cycloalkyl groups of this invention can be optionally substituted with 1–5 substituents independently selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle substituting the cycloalkyl groups of this invention are substituted with 1–5 substituents independently selected from alkyl, alkoxy, carboxy, azido, carboxaldehyde, halo, hydroxy, perfluoroalkyl, and perfluoroalkoxy.

The term "cycloalkylsulfinyl," as used herein, refers to a cycloalkyl group, as defined herein, attached to the parent molecular group through an —S(O)— group.

The term "cycloalkylsulfonyl," as used herein, refers to a cycloalkyl group, as defined herein, attached to the parent molecular group through an —SO₂— group.

The term "cycloalkylalkyl," as used herein, refers to an alkyl group, as defined herein, to which is attached at least one cycloalkyl substituent.

The term "cycloalkylalkenyl," as used herein, refers to an alkenyl group, as defined herein, to which is attached at least one cycloalkyl substituent.

The term "cyclothioalkoxy," as used herein, refers to a cycloalkyl group, as defined herein, attached to the parent molecular group through a sulfur atom.

The term "halo" as used herein, refers to F, Cl, or Br.

The term "haloalkyl," as used herein, refers to an alkyl group, as defined herein, to which is attached at least one halo substituent.

The term "haloalkenyl," as used herein, refers to an alkenyl group, as defined herein, to which is attached at least one halo substituent.

The term "heteroaryl," as used herein, refers to cyclic, aromatic five- and six-membered groups, wherein at least one atom is selected from the group consisting of N, O, and S, and the remaining atoms are carbon. The five-membered rings have two double bonds, and the six-membered rings have three double bonds. The heteroaryl groups of the invention are connected to the parent molecular group through a substitutable carbon or nitrogen in the ring. Heteroaryls are exemplified by furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, pyrazolyl, triazinyl, and the like. The heteroaryl groups of this invention can be fused to an aryl group, a heterocycle, or another heteroaryl. The heteroaryl groups of this invention can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkylsulfonyl, alkylsulfonylalkyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. The substituted aryl, heteroaryl, and heterocycle substituting the heteroaryl groups of this invention are substituted with at least one substituent selected from alkyl, alkoxy, carboxy, azido, carboxaldehyde, halo, hydroxy, perfluoroalkyl, and perfluoroalkoxy.

The term "heteroarylalkyl," as used herein, refers to an alkyl group, as defined herein, to which is attached at least one heteroaryl substituent.

The term "heteroarylalkenyl," as used herein, refers to an alkenyl group, as defined herein, to which is attached at least one heteroaryl substituent.

The term "(heteroaryl)oyl," as used herein, refers to a heteroaryl group, as defined herein, attached to the parent molecular group through a carbonyl.

The term "heterocycle," as used herein, refers to cyclic, non-aromatic, four-, five-, six-, or seven-membered rings containing at least one atom selected from the group consisting of oxygen, nitrogen, and sulfur. The four-membered rings have zero double bonds, the five-membered rings have zero or one double bonds, and the six- and seven-membered rings have zero, one, or two double bonds. Heterocycle groups of the invention are exemplified by dihydropyridinyl, morpholinyl, piperazinyl, pyrrolidinyl, tetrahydropyridinyl, piperidinyl, thiomorpholinyl, 1,3-dioxolanyl, 1,4-dioxanyl, 1,3-dioxanyl, and the like. The heterocycle groups of this invention can be fused to an aryl group or a heteroaryl group. The heterocycle groups of the invention are connected to the parent molecular group through a substitutable carbon or nitrogen atom in the heterocycle ring or the aryl or heroaryl ring to which it is fused. The heterocycle groups of this invention can be optionally substituted with 1–5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. The substituted aryl, heteroaryl, and heterocycle groups substituting the heterocycle groups of this invention are substituted with at least one substituent selected from alkyl, alkoxy, carboxy, azido, carboxaldehyde, halo, hydroxy, perfluoroalkyl, and perfluoroalkoxy.

The term "(heterocycle)alkyl," as used herein, refers to an alkyl group, as defined herein, to which is attached at least one heterocycle substituent.

The term "(heterocycle)oxy," as used herein, refers to a heterocycle, as defined herein, connected to the parent molecular group through an oxygen atom.

The term "(heterocycle)oxycarbonyl," as used herein, refers to a (heterocycle)oxy group, as defined herein, connected to the parent molecular group through a carbonyl group.

The term "(heterocycle)sulfinyl," as used herein, refers to a heterocycle group, as defined herein, connected to the parent molecular group through an —S(O)— group.

The term "(heterocycle)sulfonyl," as used herein, refers to a heterocycle group, as defined herein, connected to the parent molecular group through an —SO₂— group.

The term "hydroxy," as used herein, refers to —OH or a derivative thereof formed by replacement of the hydrogen atom thereon with a hydroxy protecting group.

The term "hydroxyalkyl," as used herein, refers to an alkyl group, as defined herein, to which is attached at least one hydroxy substituent.

The term "hydroxyalkenyl," as used herein, refers to an alkenyl group, as defined herein, to which is attached at least one hydroxy substituent.

The term "hydroxy protecting group," as used herein, refers to selectively introducible and removable groups which protect hydroxy groups against undesirable side reactions during synthetic procedures. Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)-ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, tert-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Hydroxy protecting group can also be used as prodrug-forming groups.

The term "oxo," as used herein, refers to a group formed by the replacement of two hydrogen atoms on the same carbon atom with a single oxygen atom.

The term "perfluoroalkoxy," as used herein, refers to a perfluoroalkyl group attached to the parent group through an oxygen atom.

The term "perfluoroalkoxyalkyl," as used herein, refers to an alkyl group, as defined herein, to which is attached at least one perfluoroalkoxy substituent.

The term "perfluoroalkoxyalkenyl," as used herein, refers to an alkenyl group, as defined herein, to which is attached at least one perfluoroalkoxy substituent.

The term "perfluoroalkyl," as used herein, refers to an alkyl group in which all of the hydrogen atoms have been replaced with fluorine atoms.

The term "thioalkanoyl," as used herein, refers to an alkyl group, as defined herein, connected to the parent molecular group through a thiocarbonyl.

The term "thioalkoxy," as used herein, refers to an alkyl group, as defined herein, attached to the parent molecular group through a sulfur atom.

The term "thioalkoxyalkyl," as used herein, refers to an alkyl group, as defined herein, to which is attached at least one thioalkoxy substituent.

The term "thioalkoxyalkenyl," as used herein, refers to an alkenyl group, as defined herein, to which is attached at least one thioalkoxy substituent.

The term "thiocarbonyl," as used herein, refers to —C(=S)—.

The term "thiocycloalkenyloxy," as used herein, refers to a cycloalkenyl group, as defined herein, attached to the parent molecular group through a sulfur atom.

The compounds of the invention can exist as therapeutically acceptable salts. The term "therapeutically acceptable salt," as used herein, refers to salts or zwitterionic forms of the compounds of the invention which are water or oil-soluble or dispersible, which are suitable for treatment of diseases without undue toxicity, irritation, and allergic response, which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, palmoate, pectinate, persulfate, 3-phenylpropionate, picrate, pivalate, propionate, succinate, tartrate, trichloroacetic, trifluoroacetic, phosphate, glutamate, bicarbonate, para-toluenesulfonate, and undecanoate. Also, amino groups in the compounds of the invention can be quaternized with as methyl, ethyl, propyl, and butyl chlorides, bromides and iodides; dimethyl, diethyl, dibutyl, and diamyl sulfates; decyl, lauryl, myristyl, and stearyl chlorides, bromides, and iodides; benzyl and phenethyl bromides. Examples of acids which can be employed to form therapeutically acceptable acid addition salts include inorganic acids such as hydrochloric, hydrobromic, sulphuric, and phosphoric and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary or tertiary amine. Therapeutically acceptable salts cations based on lithium, sodium, potassium, calcium, magnesium, and aluminum and non-toxic quaternary ammonia and amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "sulfonyl," as used herein, refers to —SO$_2$—.

In accordance with pharmaceutical compositions and methods of treatment, the compounds can be administered alone or in combination with other antibacterial, anti-psoriasis, anti-arthritis, and anti-chemotherapeutic toxicity agents. The therapeutically effective dose level depends on factors such as the disorder being treated and the severity of the disorder; the activity of the compound used; the composition employed; the age, body weight, general health, sex, and diet of the patient; the time of administration; the route of administration; the rate of excretion of the compound; the duration of treatment; and drugs used in combination with or coincidentally with the compounds. The compounds can be administered orally, parenterally, nasally, rectally, vaginally, or topically in unit dosage formulations containing therapeutically acceptable excipients such as carriers, adjuvants, diluents, vehicles, or combinations thereof. The term "parenteral" includes infusion, subcutaneous, intravenous, intramuscular, and intrasternal injection.

The antibacterial, anti-psoriasis, anti-arthritis, and anti-chemotherapeutic toxicity effect of parenterally administered compounds can be controlled by slowing their absorption, such as, for example, by administration of injectable suspensions of crystalline, amorphous, or otherwise water-insoluble forms of the compounds; administration of the compounds as oleaginous solutions or suspensions; or administration of microencapsulated matrices of the compounds trapped within liposomes, microemulsions, or biodegradable polymers. In each case, the ratio of compound to excipient and the nature of the excipient influences the rate of release of the compound. Transdermal patches also provide controlled delivery of compounds using rate-controlling membranes. Conversely, absorption enhancers can be used to increase absorption of the compounds.

Solid dosage forms for oral administration of the compounds include capsules, tablets, pills, powders, and granules. These compositions can contain diluents, lubricants, and buffering agents. Tablets and pills can be prepared with release-controlling coatings, and sprays can optionally contain propellants.

Liquid dosage forms for oral administration of the compounds include emulsions, microemulsions, solutions, suspensions, syrups, and elixirs. These compositions can also contain adjuvants such as wetting, emulsifying, suspending, sweetening, flavoring, and perfuming agents.

Topical dosage forms of the compounds include ointments, pastes, creams, lotions, gels, powders, solutions, sprays, and inhalants. Suppositories for rectal or vaginal administration comprise compounds with a suitable nonirritating excipient. Ophthalmic formulations such as eye drops and eye are also contemplated as being within the scope of this invention.

The total daily dose of the compounds administered to a patient in single or divided doses can be in amounts from about 0.1 to about 200 mg/kg body weight or preferably from about 0.25 to about 100 mg/kg body weight. Single dose compositions contain these amounts or submultiples thereof to make up the daily dose.

Determination of Antibacterial Activity

The minimum inhibitory concentrations (MIC's) of the compounds for the microorganisms listed in Table I were determined by the procedure described in *National Committee for Clinical Laboratory Standards. 2000. Methods for Dilution Antimicrobial Susceptibility Tests for Bacteria That Grow Aerobically*, 5th ed. Approved Standard: M7-A5 (NCCLS, Wayne, Pa.). Briefly, the compounds were dissolved in DMSO to 2 mg/mL and diluted in the appropriate susceptibility test medium to a concentration of 256 µg/mL. Serial two-fold dilutions were made in microtiter plates to achieve a final volume of 50 µL. Inocula for each organism were prepared by making a standard suspension in sterile saline with turbidity equivalent to that of a 0.5 McFarland Standard from an 18 to 24 hour culture grown on agar plates at 35° C. The standard suspension of each organism was diluted 100-fold in the appropriate medium and further diluted 2-fold by adding 50 µL to the medium containing antibiotic to achieve a final density of $5 \times 10^5$ CFU/mL. Microdilution plates were incubated for 16 to 20 hours at 35° C. in ambient air. Each plate was visually inspected, and MIC's were recorded as the lowest concentration of drug which yielded no growth, a slight haze, or sparsely isolated colonies on the inoculum spot as compared to the growth control. The compounds inhibited the growth of these bacteria with MIC's in a range of about 1 µg/mL to about 64 µg/mL; in a more preferred range, the compounds inhibited the growth of bacteria with MIC's in a range of about 8 µg/mL to about 8 µg/mL; and in a most preferred range, the compounds inhibited the growth of bacteria with MIC's in a range of about 1 µg/mL to about 4 µg/mL.

Thus, the compounds are useful for treating bacterial infections for which these microorganisms are responsible.

TABLE 1

| Microorganism |
| --- |
| *Staphylococcus aureus* NCTC10649M |
| *Staphylococcus epidermidis* 3519 |

TABLE 1-continued

| Microorganism |
| --- |
| *Moraxella catarrhalis* 2604 |
| *Enterococcus faecium* ATCC GYR 1632 |
| *Streptococcus pneumonia* ATCC6303 |

Preparation of the Compounds of the Invention

The compounds can be prepared by employing reactions shown in Schemes 1–4. It will be readily apparent to one of ordinary skill in the art that the compounds can be synthesized by substitution of the appropriate reactants in these syntheses, and that the steps themselves can be conducted in varying order. It will also be apparent that protection and deprotection steps can be performed to successfully complete the syntheses of the compounds. A thorough discussion of protecting groups is provided in *Protective Groups in Organic Synthesis*, 3rd edition, John Wiley & Sons, New York (1999).

Abbreviations used in the schemes and the examples are as follows: BINAP for 2,2'-bis(diphenylphosphino)-1,1'-binaphthyl; DME for dimethoxyethane; DMF for N,N-dimethylformamide; DMSO for dimethylsulfoxide; m-CPBA for meta-chloroperbenzoic acid; THF for tetrahydrofuran; PCC for pyridinium chlorochromate; PDC for pyridinium dichromate; DEAD for diethyl azodicarboxylate; DIAD for diisopropyl azodicarboxylate.

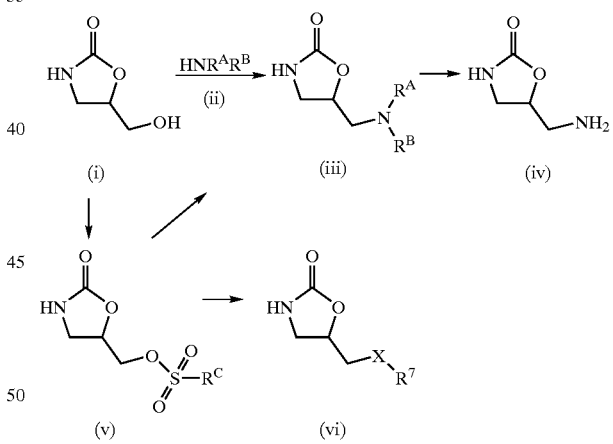

Scheme 1

Conversion of 5-(hydroxymethyl)-1,3-oxazolidin-2-one (i) to compounds of formula (v) can be accomplished by treatment of the former with a hydroxyl activating group precursor such as para-toluenesulfonyl chloride ($R^C$ is 4-methylphenyl), methanesulfonyl chloride ($R^C$ is methyl), 2-nitrobenzenesulfonyl chloride ($R^C$ is 2-nitrophenyl), or trifluoromethanesulfonyl chloride ($R^C$ is trifluoromethyl) and a base such as diisopropylethylamine, pyridine, triethylamine, sodium carbonate, potassium carbonate, or cesium carbonate, followed by treatment of the compounds of formula (v) with the appropriate $R^4$ introduction agent. For example, compounds of formula (vi) can be obtained by treatment of compounds of formula (v) with compounds of formula $(M)^+(XR^7)$ wherein M is lithium, sodium or potassium, and X is O or S. The reactions are conducted at about 0° C. to about 30° C.; and the reaction times are from about 1 to about 24 hours. Solvents useful for this reaction include benzene, toluene, THF, dioxane, DME, or mixtures thereof.

Conversion of compounds of formula (vi), wherein X is S, to compounds wherein X is S(O) or $SO_2$ can be accomplished by treatment of the former with a oxidizing agent such as m-CPBA, potassium permanganate, or potassium peroxymonosulfate (Oxone®). The reactions are conducted at about 0° C. to about 30° C.; and the reaction times are from about 1 to about 10 hours, each depending on the degree of oxidation desired. Solvents useful for this reaction include benzene, toluene, THF, dioxane, dichloromethane, chloroform, DME, or mixtures thereof.

Conversion of compounds of formula (v) to compounds of formula (iii) can be accomplished by treatment of the former with an excess of the appropriately substituted amine wherein $R^A$ and $R^B$ are independently selected from hydrogen or unsubstituted or substituted alkyl, aryl, arylalkyl, cycloalkyl, cycloalkylalkyl, heteroaryl, and heteroarylalkyl. The reactions are conducted at about 20° C. to about 110° C.; and the reaction times are from about 1 to about 24 hours. Solvents useful for this reaction include the amines themselves, benzene, toluene, THF, dioxane, acetonitrile, DME, DMSO, or mixtures thereof.

Conversion of compounds of formula (v) to compounds of formula (iii) can be accomplished by treatment of the former with compounds of formula $(M)^+(NR^AR^B)^-$ wherein $R^A$ and $R^B$, together with the nitrogen to which they are attached, are phthalimide and M is Na or K. The reactions are conducted at about 0° C. to about 50° C.; and the reaction times are from about 1 to about 24 hours. Solvents useful for this reaction include dichloromethane, toluene, THF, dioxane, DME, DMF, or mixtures thereof.

Conversion of compounds of formula (i) to compounds of formula (iii) can also be accomplished by treatment of the former with phthalimide under Mitsunobu conditions (triphenylphosphine and DEAD or DIAD). The reactions are conducted at about −10° C. to about 30° C.; and the reaction times are from about 1 to about 10 hours. Solvents useful for this reaction include benzene, toluene, THF, dioxane, DME, dichloromethane, chloroform, or mixtures thereof.

Conversion of compounds of formula (iii), wherein $R^A$ and $R^B$, together with the nitrogen to which they are attached, are phthalimide, to compounds of formula (iv) can be accomplished by treatment of the former with hydrazine. The reactions are conducted at about 50° C. to about 110° C.; and the reaction times are from about 1 to about 10 hours. Solvents useful for this reaction include ethanol, toluene, THF, dioxane, DME, or mixtures thereof.

Scheme 2

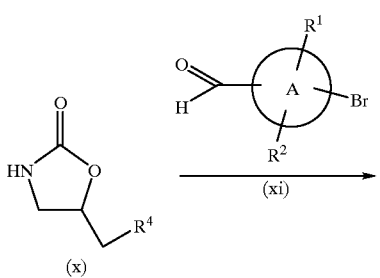

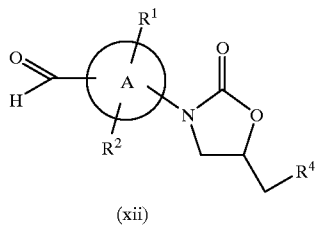

Conversion of compounds of formula (x) to compounds of formula (xii) can be accomplished by treatment of the former with compounds of formula (xi), a palladium catalyst such as tris(dibenzylideneacetone)dipalladium, palladium (II) acetate, bis(triphenylphosphine)palladium(II) chloride, or tetrakis(triphenylphosphine)palladium, and, optionally, an additive such as tributylphosphine, triphenylphosphine, (2-(diphenylphosphino)ethyl)(diphenyl)phosphine, (3-(diphenylphosphino)propyl)(diphenyl)phosphine, tri-tert-butylphosphine or BINAP, and a base such as sodium carbonate, potassium carbonate, or cesium carbonate. The reactions are conducted at about 50° C. to about 110° C.; and the reaction times are from about 1 to about 24 hours. Solvents useful for this reaction include benzene, toluene, THF, dioxane, DME, water or mixtures thereof.

As shown in Scheme 3, conversion of compounds of formula (xii) to compounds of formula (xiii) can be accomplished by treatment of the former with carbon tetrabromide and triphenylphosphine or polystyrene-supported triphenylphosphine. The reactions are typically conducted at about −15° C. to about 0° C.; and the reaction times are typically from about 1 to about 5 hours. Solvents useful for this reaction include dichloromethane, and chloroform.

Conversion of compounds of formula (xiii) to compounds of formula (Ib) can be accomplished by treatment of the former with compounds of formula $M^1$—$R^3$ ($M^1$ is trialkyl or triarylstannyl, boronic acid or ester, zinc, or zirconium; and $R^3$ is unsubstituted or substituted aryl, unsubstituted or substituted heteroaryl, unsubstituted or substituted alkenyl, or unsubstituted or substituted cycloalkenyl), a palladium catalyst such as tris(dibenzylideneacetone)dipalladium, trans-dichlorobis(triphenylphosphine)palladium(II), palladium(II)acetate or tetrakis(triphenylphosphine) palladium, and, optionally, an additive such as tributylphosphine, triphenylphosphine, triphenylarsine, tri-t-butylphosphine, tri-2-furylphosphine (2-(diphenylphosphino)ethyl)(diphenyl)phosphine, (3-(diphenylphosphino)propyl)(diphenyl)phosphine, or BINAP, and a base such as sodium carbonate, potassium carbonate, or cesium carbonate. The reactions are conducted at about 50° C. to about 110° C.; and the reaction times are from about 1 to about 48 hours. Solvents useful for this reaction include benzene, toluene, THF, dioxane, DME, water or mixtures thereof.

Scheme 3

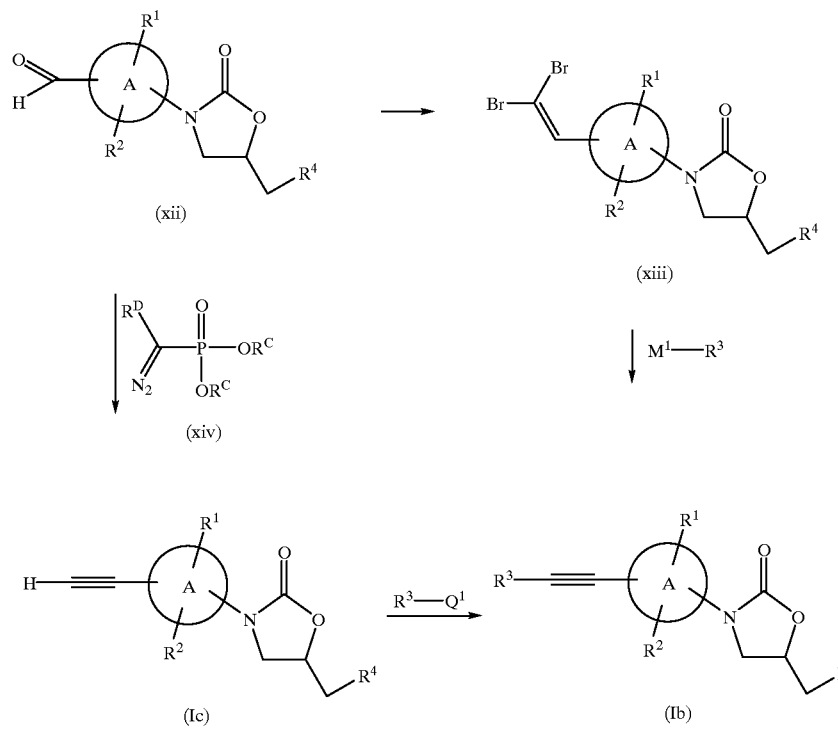

Conversion of compounds of formula (xii) to compounds of formula (Ic), can be accomplished by treatment of the former with compounds of formula (xiv) (where $R^C$ is methyl or ethyl and $R^D$ is H or alkanoyl), a base such as potassium tert-butoxide, sodium tert-butoxide, potassium carbonate, sodium carbonate, potassium bis(trimethyl)silyl amide in a solvent such as methanol, THF, dioxane or mixtures thereof. The reactions are typically conducted at about −78° C. to about 40° C.; and the reaction times are typically from about 1 to about 36 hours (*Synth. Commun.* 1989, 19, 561–564 and *J. Org. Chem.* 1971, 36, 1379–1385).

Conversion of compounds of formula (Ic) to compounds of formula (Ib) can be accomplished by treatment of the former with compounds of formula $R^3$—$Q^1$ ($R^3$ is unsubstituted or substituted alkenyl, unsubstituted or substituted cycloalkenyl, unsubstituted or substituted aryl or unsubstituted or substituted heteroaryl, and $Q^1$ is bromide, iodide, or trifluoromethanesulfonate), a palladium catalyst such as tris(dibenzylideneacetone)dipalladium, palladium(II) acetate, trans-dichlorobis(triphenylphosphine)palladium(II), or tetrakis(triphenylphosphine)palladium, and, optionally, an additive such as triphenylphosphine or tri-tert-butylphosphine and optionally a co-catalyst such as copper (I) iodide and optionally a base such as n-butyl amine, diethyl amine, triethyl amine, diusopropyl arine, or piperidine. The reactions are conducted at about 25° C. to about 110° C.; and the reaction times are from about 1 to about 48 hours. Solvents useful for this reaction include toluene, DMF, THF, N-methyl pyrrolidine, dioxane, diethyl ether or mixtures thereof.

Scheme 4

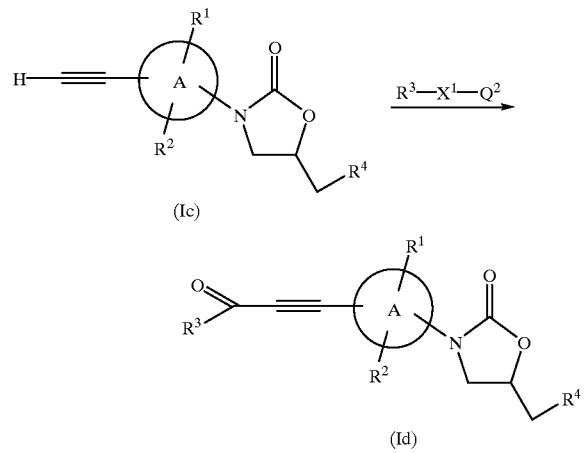

Conversion of compounds of formula (Ic) to compounds of formula (Id), can be accomplished by treatment of the former with a base such as n-butyl lithium, lithium diisopropylamide, sodium bis(trimethyl)silyl amide, lithium bis(trimethyl)silyl amide then with compounds of formula $R^3$—$X^1$—$Q^2$ (wherein $Q^2$ is Cl, Br, I, arylsulfonate or alkylsulfonate and $X^1$ is a covalent bond or C(O)), in a solvent such as THF, DME, dioxane or mixtures thereof. The reactions are typically conducted at about −78° C. to about 40° C.; and the reaction times are typically from about 1 to about 24 hours.

In addition to the chemistry discussed above, other standard manipulations can be used to prepare compounds of the invention. Amino groups can be reacted with acid chlorides, acid anhydrides, isocyanates, chloroformates, and aldehydes under reductive alkylation conditions (sodium borohydride, sodium cyanoborohydride) to provide variety of substituent groups. Carboxamido groups can be reacted with Lawesson's reagent or $P_4S_{10}Na_2CO_3$ to provide thioamides.

Heteroaryl substituents such as furan or thiazole can be converted to carboxylic acids by hydrolytic or oxidative means well-known in the art. Once formed, the carboxylic acid groups can be converted to alkoxycarbonyl, carboxamide, or cyano groups by esterification, coupling, and dehydration procedures.

A thorough discussion of reactions are described in Larock, *Comprehensive Organic Transformations. A Guide to Functional Group Preparations*, John Wiley & Sons (1999).

The invention will now be described in connection with preferred embodiments of Schemes 1–4, which are not intended to limit its scope. On the contrary, the invention covers all alternatives, modifications, and equivalents which are included within the scope of the claims. Thus, the following examples show an especially preferred practice of the invention, it being understood that the examples are for the purposes of illustration of certain preferred embodiments and are presented to provide what is believed to be the most useful and readily understood description of its procedures and conceptual aspects.

EXAMPLE 1

N-(((5S)-3-(3-fluoro-4-(4-(carbomethoxyphenyl) ethynyl)phenyl)-2-oxo-1,3-oxazolidin-5-yl)methyl) acetamide

EXAMPLE 1A ((5R)-2-oxo-1,3-oxazolidin-5-yl)methyl 4-methylbenzenesulfonate

A solution of(5R)-5-(hydroxymethyl)-1,3-oxazolidin-2-one (10.0 g), prepared as described in *Tetrahedron: Asymmetry* 1995, 6, 1181–1190, in pyridine (60 mL) at –10° C. was treated with para-toluenesulfonyl chloride (21.2 g), stirred for 2 hours, poured into 1:1 brine/water (100 mL), and extracted with ethyl acetate. The extract was washed with 1:1 saturated sodium bicarbonate/water and 1:1 brine/water, and the washes were back extracted with ethyl acetate. The combined extracts was dried (MgSO$_4$), filtered, and concentrated to provide the desired product. MS (ESI (+)) m/e 272 (M+H)$^+$; $^1$H NMR (300 MHz, CDCl$_3$) δ 7.80 (d, 2H), 7.39 (d, 2H), 4.80 (m, 1H), 4.18 (d, 2H), 3.70 (t, 1H), 3.50 (dd, 1H), 2.45 (s, 3H).

EXAMPLE 1B 2-(((5R)-2-oxo-1,3-oxazolidin-5-yl)methyl)-1H-isoindole-1,3(2H)-dione A solution of Example IA (22.16 g) in DMF (163 mL) at room temperature was treated with potassium phthalimide (16.7 g), heated to 80° C., stirred for 5 hours, poured into 1:1 brine/water (200 mL), and extracted with dichloromethane. The extract was dried (MgSO$_4$), filtered, and concentrated. The concentrate was treated with ethyl acetate (200 mL), cooled to 5° C., and filtered. The mother liquor was concentrated, treated with ethyl acetate (100 mL), cooled to 5° C., filtered, and combined with the first crop to provide the desired product. MS (ESI(+)) m/e 247 (M+H)$^+$; $^1$H NMR (300 MHz, CDCl$_3$) δ 7.88 (m, 2H), 7.75 (m, 2H), 4.98 (m, 1H), 4.10 (dd, 1H), 3.90 (dd, 1H), 3.73 (t, 1H), 3.49 (dd, 1H).

EXAMPLE 1C 4-((5S)-5-((1,3-dioxo-1,3-dihydro-2H-isoindol-2-yl) methyl)-2-oxo-1,3-oxazolidin-3-fluorobenzaldehyde A suspension of Example 1B (2.5 g) in toluene (20 mL) in a sealable tube was degassed with nitrogen and treated with 4-bromo-2-fluorobenzaldehyde (2.03 g), BINAP (498 mg), cesium carbonate (4.56 g), and tris (dibenzylideneacetone)dipalladium (366 mg). The tube was sealed, and the mixture was heated at 100° C. for 24 hours, cooled, poured into 1:1 saturated ammonium chloride/water (200 mL), and extracted with ethyl acetate. The extract was dried (MgSO$_4$), filtered, and concentrated. The concentrate was treated with dichloromethane (100 mL), cooled to 5° C., and filtered. The filtrate was concentrated, treated with dichloromethane (70 mL), cooled to 5° C., filtered, and combined with the first crop to provide the desired product. mp 167–169° C.; MS (ESI(+)) m/e 369 (M+H)$^+$; $^1$H NMR (300 MHz, CDCl$_3$) δ 10.27 (s, 1H), 7.88 (m, 3H), 7.75 (m, 2H), 7.63 (dd, 1H), 7.27 (dd, 1H), 5.04 (m, 1H), 4.16 (m, 2H), 4.00 (m, 2H).

EXAMPLE 1D 2-(((5S)-3-(4-(2,2-dibromovinyl)-3-fluorophenyl)-2-oxo-1,3-oxazolidin-5-yl)methyl)-1H-isoindole-1,3 (2H)-dione Polymer-supported triphenylphosphine (10.0 g of 3 mmol/g, 2% divinylbenzene cross-linked polystyrene resin) was swelled in dichloromethane (100 mL) and cooled to –10° C. The mixture was treated with carbon tetrabromide (4.97 g), warmed to –5° C., stirred for 30 minutes, treated portionwise with Example 1C (1.84 g), stirred for 20 minutes, treated with methanol (50 mL) and filtered. The resin was washed with dichloromethane (100 mL), 1:1 dichloromethane/methanol (100 mL), and methanol (3×100 mL). The washes were combined, and the solution was concentrated. The concentrate was dissolved in dichloromethane (150 mL) and washed with 1:1 saturated sodium bicarbonate/water and 1:1 brine/water. The aqueous washes were back extracted with dichloromethane and the combined extracts were dried (MgSO$_4$), filtered, and concentrated to provide the desired product. MS (ESI(+)) m/e 542 (M+NH$_4$)$^+$; $^1$H NMR (300 MHz, CDCl$_3$) δ 7.89 (m, 2H), 7.77 (m, 3H), 7.50 (s, 1H), 7.46 (dd, 1H), 7.23 (dd, 1H), 5.01 (m, 1H), 4.16 (m, 2H).

EXAMPLE 1E

N-(((5S)-3-(4-(2,2-dibromovinyl)-3-fluorophenyl)-2-oxo-1,3-oxazolidin-5-yl)methyl)acetamide A suspension of Example 1D (2.45 g) in 1:1 THF/ethanol (36 mL) was heated to 70° C., and treated with hydrazine monohydrate (3×227 µL) at 1 hour intervals. One hour after the final addition, the mixture was cooled to 25° C., and filtered. The filtrate was concentrated, dissolved in a mixture of pyridine (10 mL) and dichloromethane (25 mL), cooled to –5° C., treated with acetic anhydride (880 µL), warmed to room temperature, stirred for 5 minutes, and concentrated to provide crude product. The crude product was dissolved in 4:1 THF/dichloromethane (75 mL) and washed with 1:1 brine/water. The aqueous wash was extracted with dichloromethane (25 mL), and the combined extracts were dried over MgSO$_4$. Next the mixture was filtered and concentrated. The residue was dissolved in acetone (20 mL) and filtered. The filtrate was concentrated and the residue triturated with hexanes to provide the desired product. mp 177–179° C.; MS (ESI(+)) m/e 437 (M+H)+; 1H NMR (300 MHz, CDCl3) δ 7.81 (t, 1H), 7.50 (s, 1H), 7.47 (dd, 1H), 7.20 (dd, 1H), 5.92 (br t, 1H), 4.80 (m, 1H), 4.06 (t, 1H), 3.77 (dd, 1H), 3.75–3.55 (m, 2H), 2.02 (s, 3H).

EXAMPLE 1F methyl 4-((4-((5 S)-5-((acetylamino)methyl)-2-oxo-1,3-oxazolidin-3-yl)-2-fluorophenyl)ethynyl) benzoate A mixture of Example 1E (55 mg), 4-metboxycarbonylphenylboronic acid (27.2 mg), and tris(dibenzylideneacetone)dipalladium (15 mg) in degassed dimethoxyethane (1.3 mL) was treated with 2N aqueous Na2CO3 (0.1 mL), heated to 70° C. for 20 hours, and concentrated. The concentrate was dissolved in dichloromethane (2 mL), filtered, and concentrated. The concentrate was purified by flash column chromatography on silica gel with 1:1 hexanes/acetone to provide the desired product. MS (ESI(+)) m/e 411 (M+H)+; MS (ESI(−)) m/e 409 (M−H)−; 1H NMR (300 MHz, CDCl3) δ 8.00 (d, 2H), 7.61 (d, 2H), 7.55 (dd, 1H), 7.50 (t, 1H), 7.20 (dd, 1H), 6.0 (br t, 1H), 4.80 (m, 1H), 4.07 (t, 1H), 3.93 (s, 3H), 3.85–3.75 (dd, 1H), 3.60–3.50 (m, 2H), 2.05 (s, 3H).

EXAMPLE 2

N-(((5S)-3-(3-fluoro-4-(1H-pyrrol-2-ylethynyl) phenyl)-2-oxo-1,3-oxazolidin-5-yl)methyl)acetamide The desired product was prepared by substituting 1-(tert-butoxycarbonyl)-pyrrole-2-boronic acid for 4-methoxycarbonylphenylboronic acid in Example 1F to afford the tert-butoxycarbonyl-bromo olefin which was treated with sodium methoxide in methanol (0.25 mL) for 10 minutes and concentrated. The concentrate was purified by flash column chromatography on silica gel with 97:3 dichloromethane/methanol to provide the desired product. MS (ESI(+)) m/e 342 (M+H)+; 1H NMR (300 MHz, CD3OD) δ 7.56 (dd, 1H), 7.46 (t, 1H), 7.27 (dd, 1H), 6.78 (m, 1H), 6.43 (dd, 1H), 6.12 (dd, 1H), 4.80 (m, 1H), 4.15 (t, 1H), 3.82 (dd, 1H), 3.56 (d, 2H), 1.96 (s, 3H).

EXAMPLE 3

N-(((5S)-3-(3-fluoro-4-(7H-purin-6-ylethynyl) phenyl)-2-oxo-1,3-oxazolidin-5-yl)methyl)acetamide

EXAMPLE 3A 2-(3-(4-Ethynyl-3-fluoro-phenyl)-2-oxo-oxazolidin-5-ylmethyl)-isoindole-1,3-dione To a −78° C. solution of potassium t-butoxide (7.7 mL of a 1.0 M solution in THF) was added a −78° C. THF (4 mL) solution of dimethyl diazomethylphosphonate (1.15 g, prepared according to the procedure described in *J. Org. Chem.* 1971, 36, 1379–1385). The mixture was stirred at −78° C. for 10 minutes, then a −78° C. solution of Example 1C (2.18 g) in THF (100 mL) was added via cannula over 20 minutes. The reaction mixture was stirred for 24 hours gradually warming to room temperature. The mixture was quenched with 1:1 saturated ammonium chloridel water (100 mL) and extracted with dichloromethane (50 mL). The aqueous layer was extracted with 4:1 THF/dichloromethane (3×100 mL). The combined extracts were washed with 1:1 saturated sodium bicarbonate/water (100 mL), and then with 1:1 brine/water (100 mL). The organic extracts were dried over MgSO4, filtered, and concentrated to provide crude product. The crude product was purified by flash column chromatography on silica gel with 98:2 dichloromethane/methanol to provide the desired product.MS (ESI(+)) m/e 365 (M+H)+; 1H NMR (300 MHz, DMSO) δ 7.85–7.95 (m, 4H), 7.45–7.64 (m, 2H), 7.25–7.35 (dd, J=2.1, 8.7 Hz, 1H), 4.97 (m, 1H), 4.22 (t, J=9 Hz 4.1 (m, 3H), 3.30 (s, 1H).

EXAMPLE 3B

N-(((5S)-3-(4-ethynyl-3-fluorophenyl)-2-oxo-1,3-oxazolidin-5-yl)methyl)acetamide A 50° C. suspension of Example 3A (1.65 g) in 1:1 THF/ethanol (34 mL) was treated with hydrazine monohydrate (3×240 μL) at 1 hour intervals. One hour after the final addition the mixture was cooled to 25° C. and filtered. The filtrate was concentrated in vacuo. The resultant material was dissolved in a mixture of pyridine (17 mL) and dichloromethane (17 mL), cooled to −5° C., and treated with acetic anhydride (854 μL). The reaction mixture was warmed to room temperature, stirred for 5 minutes, and concentrated to provide crude product. The crude product was dissolved in 4:1 THF/dichloromethane (75 mL) and washed with 1:1 brine/water. The aqueous wash was extracted with dichloromethane (25 mL), and the combined extracts were dried over MgSO4. Next the mixture was filtered and concentrated. The residue was dissolved in acetone (20 mL) and filtered. The filtrate was concentrated and the residue triturated with hexanes to provide the desired product. MS (ESI(+)) m/e 277 (M+H)+; 1H NMR (300 MHz, CDCl3) δ 7.5–7.4 (m, 2H), 7.16–7.19 (dd, J=2.4, 8.4 Hz, 1H), 5.93 (bt, 1H), 4.8 (m, 1H), 4.05 (t, J=9 Hz, 1H), 3.8–3.6 (m, 3H), 3.28 (s, 1H), 2.02 (s, 3H).

EXAMPLE 3C

N-(3-(3-Fluoro-4-(7H-purin-6-ylethynyl)-phenyl)-2-oxo-oxazolidin-5-ylmethl)-acetamide To a suspension of Example 3B (100 mg) and diisopropylamine (0.25 mL) in degassed DMF (1 mL) was added sequentially 6-iodopurine (89 mg), copper iodide (3.5 mg) and tetrakis(triphenylphosphine)palladium (21 mg). The mixture was heated to 60° C. for 4 hours. Next, the reaction mixture was cooled to room temperature and concentrated. The resultant material was dissolved in dichloromethane (4 mL), then filtered. The precipitate was washed with water (10 mL), then cold acetone (3 mL) to provide the desired solid. MS (ESI(+)) m/e 395 (M+H)+; 1H NMR (300 MHz, DMSO) δ 8.91 (s, 1H), 8.69 (s, 1H), 8.25 (t, J=5.7 Hz, 1H), 7.89 (m, 1H), 7.82 (t, J=9 Hz, 1H), 7.7 (dd, J=2.1, 12.3 Hz, 1H), 7.5 (dd, J=2.1, 9 Hz, 1H), 4.78 (m, 1H), 4.19 (t, J=9 Hz, 1H), 3.8 (dd, J=6.3, 9.6 Hz, 1H), 3.44 (t, J=5.7 Hz, 2H), 1.84 (s, 3H).

EXAMPLE 4

N-(((5S)-3-(4-((5-(aminosulfonyl)thien-2-yl) ethynyl)-3-fluorophenyl)-2-oxo-1,3-oxazolidin-5-yl) methyl)acetamide The desired product was prepared as in Example 3C but with heating at 35° C. for 1 hour and substituting 5-bromothiophene-2-sulfonic acid amide for 6-iodopurine. MS (ESI (+)) m/e 438 (M+H)+; 1H NMR (300 MHz, DMSO) δ 8.24 (t, J=5.7 Hz, 1H), 7.86 (s, 2H), 7.69 (t, J=8.4 Hz, 1H), 7.65 (dd, J=1.8, 12.0 Hz, 1H), 7.52 (d, J=4.2 Hz, 1H), 7.45 (d, J=3.9 Hz, 1H), 7.42 (dd, J=1.8, 8.7 Hz, 1H), 4.76 (m, 1H), 4.16 (t, J=9 Hz, 1H), 3.78 (dd, J=6.3, 9.6 Hz, 1H), 3.42 (t, J=5.7 Hz, 2H), 1.83 (s, 3H).

EXAMPLE 5

N-(((5S)-3-(3-fluoro-4-((1-oxo-2,3-dihydro-1H-inden-5-yl)ethynyl)phenyl)-2-oxo- 1,3-oxazolidin-5-yl)methyl)acetamide The desired product was prepared as in Example 3C but with heating at 40° C. for 3 hours and substituting 5-bromo-indan-1-one for 6-iodopurine. MS (ESI(+)) m/e 407 (M+H)$^+$; $^1$H NMR (300 MHz, DMSO) δ 8.23 (t, J=5.7 Hz, 1H), 7.77 (s, 1H), 7.55–7.72 (m, 4H), 7.42 (dd, J=2.1, 9 Hz, 1H), 4.76 (m, 1H), 4.17 (t, J=9 Hz, 1H), 3.78 (dd, J=6.3, 9.6 Hz, 1H), 3.43 (t, J=5.7 Hz, 2H), 3.13 (t, J=6 Hz, 2H), 2.67 (m, 2H), 1.84 (s, 3H).

EXAMPLE 6

5-((4-(((5S)-5-((acetylamino)methyl)-2-oxo-1,3-oxazolidin-3-yl)-2-fluorophenyl)ethynyl)-2,3-dihydro-1-benzofuran-7-carboxylic acid The desired product was prepared as in Example 3C but with heating at 60° C. for 8 hours and substituting 5-bromo-2,3-dihydrobenzofuran-7-carboxylic acid for 6-iodopurine. MS (ESI(+)) m/e 461 (M+23)$^+$; $^1$H NMR (300 MHz, DMSO) δ 8.23 (t, J=6.3 Hz, 1H), 7.88 (m, 2H), 7.72 (t, J=9 Hz, 1H), 7.66 (dd, J=2.1, 12.3 Hz, 1H), 7.4 (dd, J=2.1, 9 Hz, 1H), 4.76 (m, 1H), 4.17 (t, J=9 Hz, 1H), 3.78 (dd, J=6.3, 9.6 Hz, 1H), 3.43 (t, J=5.7 Hz, 2H), 3.13 (t, J=6 Hz, 2H), 2.67 (m, 2H), 1.84 (s, 3H).

EXAMPLE 7

N-(((5S)-3-(4-((1,3-dioxo-2,3-dihydro-1H-isoindol-5-yl)ethynyl)-3-fluorophenyl)-2-oxo-1,3-oxazolidin-5-yl)methyl)acetamide The desired product was prepared as in Example 3C but with heating at 60° C. for 8 hours and by substituting 5-bromo-isoindole-1,3-dione for 6-iodopurine. MS (ESI(+)) m/e 422 (M+H)$^+$; $^1$H NMR (300 MHz, DMSO) δ 11.5 (s, 1H), 8.25 (t, J=5.7 Hz, 1H), 7.85–8.00 (m, 3H), 7.73 (t, J=8.4 Hz, 1H), 7.67 (dd, J=2.1, 12.3 Hz, 1H), 7.45 (dd, J=2.1, 8.4 Hz, 1H), 4.78 (m, 1H), 4.19 (t, J=9 Hz, 1H), 3.8 (dd, J=6.3, 9.6 Hz, 1H), 3.44 (t, J=5.7 Hz, 2H), 1.84 (s, 3H).

EXAMPLE 8

N-(((5S)-3-(4-((5-cyanopyridin-3-yl)ethynyl)-3-fluorophenyl)-2-oxo-1,3-oxazolidin-5-yl)methyl)acetamide The desired product was prepared as in Example 3C but with heating at 35° C. for 2 hours and by substituting 5-bromo-nicotinonitrile for 6-iodopurine. MS (ESI(+)) m/e 379 (M+H)$^+$; $^1$H NMR (300 MHz, DMSO) δ 9.02 (dd, J=2.1, 5.1 Hz, 2H), 8.57 (t, J=2.1 Hz, 1H), 8.23 (t, J=5.7 Hz, 1H), 7.7 (t, J=8.4 Hz, 1H), 7.67 (dd, J=2.4, 12.3 Hz, 1H), 7.4 (dd, J=2.44, 8.4 Hz, 1H), 4.76 (m, 1H), 4.17 (t, J=9 Hz, 1H), 3.78 (dd, J=6.3, 9.6 Hz, 1H), 3.43 (t, J=5.7 Hz, 2H), 1.83 (s, 3H).

EXAMPLE 9

N-(((5S)-3-(3-fluoro-4-(1,8-naphthyridin-2-ylethynyl)phenyl)-2-oxo-1,3-oxazolidin-5-yl)methyl)acetamide The desired product was prepared as in Example 3C but with heating at 60° C. for 4 hours and substituting 2-bromo-[1.8]naphthyridine for 6-iodopurine. MS (ESI(+)) m/e 405 (M+H)$^+$; $^1$H NMR (300 MHz, DMSO) δ 9.04 (dd, J=1.5, 4.2 Hz, 1H), 8.45 (t, J=8.7 Hz, 2H), 8.24 (t, J=5.7 Hz, 1H), 7.97 (d, J=8.7 Hz, 1H), 7.86 (t, J=4.5 Hz, 1H), 7.8 (t, J=8.7 Hz, 1H), 7.66 (dd, J=2.1, 12.3 Hz, 1H), 7.45 (dd, J=2.1, 8.7 Hz, 1H), 4.76 (m, 1H), 4.18 (t, J=9 Hz, 1H), 3.79 (dd, J=6.3, 9.6 Hz, 1H), 3.44 (t, J=5.7 Hz, 2H), 1.83 (s, 3H).

EXAMPLE 10

N-(((5S)-3-(3-fluoro-4-((4-(hydroxymethyl)phenyl)ethynyl)phenyl)-2-oxo-1,3-oxazolidin-5-yl)methyl)acetamide The desired product was prepared by substituting 4-hydroxymethylphenylboronic acid for 4-methoxycarbonylphenylboronic acid in Example 1F. MS (ESI(+)) m/e 383 (M+H)$^+$; $^1$H NMR (300 MHz, CDCl$_3$) δ 7.60 (dd, 1H), 7.50 (d, 2H), 7.38 (d, 2H), 7.30 (m, 2H), 4.80 (m, 1H), 4.17 (t, 1H), 3.84 (dd, 1H), 3.56 (d, 2H), 1.96 (s, 3H).

EXAMPLE 11

N-(((5S)-3-(3-fluoro-4-(1,8-naphthyridin-2-ylethynyl)phenyl)-2-oxo-1,3-oxazolidin-5-yl)methyl)acetamide

EXAMPLE 11A 2-(3-(4-Acetyl-3-fluoro-phenyl)-2-oxo-oxazolidin-5-ylmethyl)-isoindole-1,3-dione Example 1C (5 g) in dichloromethane (130 mL) was treated sequentially with diazomethane (3×60 mL of a 0.4 M solution in diethyl ether) at 24 hours intervals. The mixture was stirred at room temperature for 5 days, then concentrated and used directly in the next step.

EXAMPLE 11B 2-(3-(3-Fluoro-4-prop-1-ynyl-phenyl)-2-oxo-oxazolidin-5-ylmethyl)-isoindole- 1,3-dione To a −78° C. solution of potassium t-butoxide (17 mL of a 1.0 M solution in THF) was added a −78° C. THF (4 mL) solution of dimethyl diazomethylphosphonate (2.53 g, prepared according to the procedure described in J. Org. Chem. 1971, 36, 1379–1385). The mixture was stirred at −78° C. for 10 minutes then a −78° C. solution of Example 3A (5.19 g) in THF (100 mL) was added via cannula over 20 minutes. The reaction mixture was stirred for 24 hours, gradually warming to room temperature. The mixture was quenched with 1:1 saturated ammonium chloride/water (200 mL) and extracted with dichloromethane (50 mL). The aqueous layer was extracted with 4:1 THF/dichloromethane (250 mL), and the combined extracts were washed with 1:1 saturated sodium bicarbonate/water (200 mL) and 1:1 brine/water (200 mL). The organic extracts were dried over MgSO$_4$, filtered, and concentrated to provide crude product. The crude product was purified by flash column chromatography on silica gel eluting with 4:1 hexanes/acetone to provide the desired product. MS (ESI(+)) m/e 379 (M+H)$^+$; $^1$H NMR (300 MHz, CDCl$_3$) δ 7.9 (m, 2H), 7.77 (m, 2H), 7.45 (dd, J=2.4, 9 Hz, 1H), 7.36 (d, J=7.2 Hz, 1H), 7.25–7.35 (dd, J=2.4, 8.7 Hz, 1H), 4.97 (m, 1H), 4.07–4.18 (m, 2H), 3.8–4.01 (m, 2H), 2.09 (s, 3H).

EXAMPLE 11C

N-(((5S)-3-(3-fluoro-4-(1,8-naphthyridin-2-ylethynyl)phenyl)-2-oxo-1,3-oxazolidin-5-yl)methyl)acetamide A 50° C. suspension of Example 11B (2.0 g) in 1:1 THF/ethanol (20 mL) was treated with hydrazine monohydrate (3×240 μL) at 1 hour intervals. One hour after the final addition, the mixture was cooled to 25° C. and filtered. The filtrate was concentrated in vacuo. The resultant material was dissolved in a mixture of pyridine (10 mL) and dichloromethane (10 mL), cooled to −5° C., and treated with acetic anhydride (990 μL). The reaction mixture was warmed to room temperature, stirred for 5 minutes, and concentrated to provide crude product. The crude product was dissolved in 4:1 THF/dichloromethane (75 mL) and washed with 1:1 brine/water. The aqueous wash was extracted with dichloromethane (25 mL), and the combined extracts were dried over $MgSO_4$. Next the mixture was filtered and concentrated. The residue was dissolved in acetone (20 mL) and filtered. The filtrate was concentrated and the residue triturated with hexanes to provide the desired product. MS (ESI(+)) m/e 291 (M+H)+; $^1$H NMR (300 MHz, DMSO) δ 8.22 (t, J=5.7 Hz, 1H), 7.56 (dd, J=2.1, 12.3 Hz, 1H), 7.47 (t, J=8.7 Hz, 1H), 7.3 (dd, J=2.1, 8.7 Hz, 1H), 4.73 (m, 1H), 4.12 (t, J=9 Hz, 1H), 3.74 (dd, J=6.3, 9.6 Hz, 1H), 3.41 (t, J=5.7 Hz, 2H), 2.07 (s, 3H), 1.83 (s, 3H).

EXAMPLE 12

N-(((5S)-3-(3-fluoro-4-((4-methoxy-3-pyridinyl) ethynyl)phenyl)-2-oxo-1,3-oxazolidin-5-yl)methyl) acetamide The desired product was prepared by substituting 2-methoxy-5-pyridineboronic acid for 4-methoxycarbonylphenylboronic acid in Example 1F. MS (ESI(+)) m/e 384 (M+H)+; $^1$H NMR (300 MHz, CDCl$_3$) δ 8.37 (d, 1H), 7.70 (dd, 1H), 7.50 (m, 1H), 7.21 (dd, 1H), 6.73 (dd, 1H), 5.91(bt, 1H), 4.79 (m, 1H), 4.07 (t, 1H), 3.97 (s, 3H), 3.81 (dd, 1H), 3.75–3.60 (m, 2H), 2.03 (s, 3H).

EXAMPLE 13

N-(((5S)-3-(4-((2-aminopyrimidin-5-yl)ethynyl)-3-fluorophenyl)-2-oxo-1,3-oxazolidin-5-yl)methyl) acetamide A solution of Example 1F (41 mg) in degassed DME (1.3 mL) was treated with 5-(4,4,5,5-tetramethyl-(1,3,2) dioxaborolan-2-yl)-pyrimidin-2-ylamine (41.5mg, prepared according to the procedure described in *Tetrahedron Letters*, 1997, 38, 3447–3450), tetrakis(triphenylphosphine) palladium (12 mg) and a degassed 2 N solution of potassium carbonate in water (0.2 mL). The tube was sealed, heated to 70° C., and stirred for 20 hours. The reaction mixture was then cooled to room temperature, concentrated, and diluted with dichloromethane (4 mL). The precipitate was removed by filtration and washed with water (10 mL) and then cold acetone (3 mL) to provide the desired product. MS (ESI(+)) m/e 370 (M+H)+; $^1$H NMR (300 MHz, MeOH) δ 8.49 (s, 2H), 7.61 (dd, J=2.1, 12 Hz, 1H), 7.57 (t, J=8.4 Hz, 1H), 7.32 (dd, J=2.1, 8.7 Hz, 1H), 4.8 (m, 1H), 4.16 (t, J=9 Hz, 1H), 3.83 (dd, J=6.3, 9.6 Hz, 1H), 3.56(d, J=5.4 Hz, 2H), 1.96 (s, 3H).

EXAMPLE 14

N-(((5S)-3-(3-fluoro-4-(pyrimidin-5-ylethynyl) phenyl)-2-oxo-1,3-oxazolidin-5-yl)methyl)acetamide The desired product was prepared as in Example 13 with substitution of 5-(4,4,5,5-tetramethyl-(1,3,2)dioxaborolan-2-yl)-pyrimidine (38.7 mg, prepared according to the procedure described in *Tetrahedron Letters*, 1997, 38, 3447–3450), for 5-(4,4,5,5-tetramethyl-(1,3,2) dioxaborolan-2-yl)-pyrimidin-2-ylamine. MS (ESI(+)) m/e 355 (M+H)+; $^1$H NMR (300 MHz, MeOH) δ 9.11 (s, 1H), 8.93 (s, 2H), 7.65 (dd, J=2.1, 12 Hz, 1H), 7.62 (t, J=8.4 Hz, 1H), 7.38 (dd, J=2.1, 8.4 Hz, 1H), 4.8 (m, 1H), 4.18 (t, J=9 Hz, 1H), 3.85 (dd, J=6.3, 9.6 Hz, 1H), 3.57(d, J=5.4 Hz, 2H), 1.96 (s, 3H).

EXAMPLE 15

N-(((5S)-3-(4-((3-aminophenyl)ethynyl)-3-fluorophenyl)-2-oxo-1,3-oxazolidin-5-yl)methyl) acetamide The desired product was prepared by substituting 3-aminophenylboronic acid hydrate for 4-methoxycarbonylphenylboronic acid in Example 1F. MS (ESI(+)) m/e 368 (M+H)+; $^1$H NMR (300 MHz, CD$_{3OD}$) δ 7.63 (dd, 1H), 7.55 (t, 1H), 7.48 (d, 2H), 7.40 (s, 1H), 7.33 (dd, 1H), 7.26 (m, 1H), 4.80 (m, 1H), 4.17 (t, 1H), 3.85 (dd, 1H), 3.57 (d, 2H), 1.96 (s, 3H).

EXAMPLE 16 methyl 3-((4-((5S)-5-((acetylamino)methyl)-2-oxo-1,3-oxazolidin-3-yl)-2-fluorophenyl)ethynyl) benzoate The desired product was prepared by substituting 3-methoxycarbonylphenylboronic acid for 4-methoxycarbonylphenylboronic acid in Example 1F. MS (ESI(+)) m/e 411 (M+H)+; $^1$H NMR (300 MHz, CDCl$_3$) δ 8.20 (t, 1H), 8.01 (d, 1H), 7.71 (d, 1H), 7.51 (s, 1H), 7.46 (m, 2H), 7.20 (dd, 1H), 6.05 (bt, 1H), 4.80 (m, 1H), 4.07 (t, 1H), 3.94 (s, 3H), 3.81 (dd, 1H), 3.75–3.60 (m, 2H), 2.04 (s, 3H).

EXAMPLE 17

N-(3-(2-(4-((5S)-5-((acetylamino)methyl)-2-oxo-1, 3-oxazolidin-3-yl)-2-fluorophenyl)ethynyl)phenyl) acetamide The desired product was prepared by substituting 3-acetamidophenylboronic acid for 4-methoxycarbonylphenylboronic acid in Example 1F. MS (ESI(+)) m/e 410 (M+H)+; $^1$H NMR (300 MHz, CDCl$_3$) δ 7.65 (m, 1H), 7.54–7.46 (m, 3H), 7.31–7.27 (m, 3H), 7.20 (dd, 1H), 5.97 (bt, 1H), 4.80 (m, 1H), 4.06 (t, 1H), 3.80 (dd, 1H), 3.75–3.60 (m, 2H), 2.19 (s, 3H), 2.03 (2, 3H).

EXAMPLE 18

N-(((5S)-3-(4-((3-(aminomethyl)phenyl)ethynyl)-3-fluorophenyl)-2-oxo-1,3-oxazolidin-5-yl)methyl) acetamide The desired product was prepared by substituting 3-aminomethylphenylboronic acid, hydrochloride for 4-methoxycarbonylphenylboronic acid in Example 1F. MS (ESI(+)) m/e 382 (M+H)+; $^1$H NMR (300 MHz, CD$_3$OD) δ 7.64 (s, 1H), 7.60–7.45 (m, 5H), 7.35 (dd, 1H), 4.80 (m, 1H), 4.20 (m, 1H), 4.14 (s, 2H), 3.84 (dd, 1H), 3.58 (m, 2H), 1.96 (s, 3H).

EXAMPLE 19

N-(((5S)-3-(3-fluoro-4-((4-hydroxyphenyl)ethynyl) phenyl)-2-oxo-1,3-oxazolidin-5-yl)methyl)acetamide The desired product was prepared by substituting 4-hydroxyphenylboronic acid, pinacol ester for 4-methoxycarbonylphenylboronic acid in Example 1F. MS (ESI(+)) m/e 386 (M+NH$_4$)$^+$; $^1$H NMR (300 MHz, CD$_3$OD) δ 7.55 (dd, 1H), 7.34 (d, 2H), 7.30 (m, 2H), 6.77 (d, 2H), 4.78 (m, 1H), 4.16 (t, 1H), 3.82 (dd 1H), 3.56 (d, 2H), 1.96 (s, 3H).

EXAMPLE 20

N-(((5S)-3-(3-fluoro-4-((2-oxo-2,3-dihydro-1,3-benzothiazol-6-yl)ethynyl)phenyl)-2-oxo-3-oxazolidin-5-yl)methyl)acetamide The desired product was prepared as in Example 3C but with heating at 60° C. for 8 hours and substituting 6-bromo-3H-benzothiazol-2-one for 6-iodopurine.MS (ESI(+)) m/e 426 (M+H)$^+$; $^1$H NMR (300 MHz, DMSO) δ 12.1 (s, 1H), 8.23 (t, J=6 Hz, 1H), 7.88 (m, 1H), 7.82 (s, 1H), 7.64 (m, 1H), 7.4 (m, 2H), 7.16 9(d, J=8.7 Hz, 1H), 4.76 (m, 1H), 4.15 (t, J=9 Hz, 1H), 3.78 (dd, J=6.3, 9.6 Hz, 1H), 3.42 (t, J=5.7 Hz, 2H), 1.83 (s, 3H.

It will be evident to one skilled in the art that the invention is not limited to the forgoing examples, and that it can be embodied in other specific forms without departing from the essential attributes thereof. Thus, it is desired that the examples be considered as illustrative and not restrictive, reference being made to the claims, and that all changes which come within the meaning and range of equivalency of the claims be embraced therein.

What is claimed is:

1. A compound selected from:

N-(((5S)-3-(3-fluoro-4-(7H-purin-6-ylethynyl)phenyl)-2-oxo-1,3-oxazolidin-5-yl)methyl)acetamide, N-(((5S)-3-(4-((5-(aminosulfonyl)thien-2-yl)ethynyl)-3-fluorophenyl)-2-oxo-1,3-oxazolidin-5-yl)methyl)acetamide, N-(((5S)-3-(3-fluoro4-((1-oxo-2,3-dihydro-1H-inden-5-yl)ethynyl)phenyl)-2-oxo-1,3-oxazolidin-5-yl)methyl)acetamide, 5-((4-((5S)-5-((acetylamino)methyl)-2-oxo-1,3-oxazolidin-3-yl)-2-fluorophenyl)ethynyl)-2,3-dihydro-1-benzofuran-7-carboxylic acid, N-(((5S)-3-(4-((1,3-dioxo-2,3-dihydro-1H-isoindol-5-yl)ethynyl)-3-fluorophenyl)-2-oxo-1,3-oxazolidin-5-yl)methyl)acetamide, N-(((5S)-3-(4-((5-cyanopyridin-3-yl)ethynyl)-3-fluorophenyl)-2-oxo-1,3-oxazolidin-5-yl)methyl)acetamide, N-(((5S)-3-(3-fluoro-4-(1,8-naphthyridin-2-ylethynyl)phenyl)-2-oxo-1,3-oxazolidin-5-yl)metyl)acetanide, N-(((5S)-3-(3-fluoro-4-(1,8-naphthyridin-2-ylethynyl)phenyl)-2-oxo-1,3-oxazolidin-5-yl)methyl)acetamide, N-(((5S)-3-(4-((2-aminopyrimidin-5-yl)ethynyl)-3-fluorophenyl)-2-oxo-1,3-oxazolidin-5-yl)methyl)acetamide, N-(((5S)-3-(3-fluoro-4-(pyrimidin-5-ylethynyl)phenyl)2-oxo-1,3-oxazolidin-5-yl)metbyl)acetamide, and N-(((5S)-3-(3-fluoro-4-((2-oxo-2,3-dihydro-1,3-benzothiazol-6-yl)ethynyl)phenyl)-2-oxo-1,3-oxazolidin-5-yl)methyl)acetamide.

* * * * *